(12) United States Patent  
Appel et al.

(10) Patent No.: US 7,835,005 B2
(45) Date of Patent: Nov. 16, 2010

(54) GAS ANALYZER SYSTEM

(75) Inventors: Dirk Appel, Salem, MA (US); Gaston E. Marzoratti, Franklin, MA (US); Shrikrishna H. Nabar, Shrewsbury, MA (US); Robert F. Mouradian, Canton, MA (US)

(73) Assignee: Thermo Fisher Scientific Inc., Waltham, MA (US)

( * ) Notice: Subject to any disclaimer, the term of this patent is extended or adjusted under 35 U.S.C. 154(b) by 237 days.

(21) Appl. No.: 12/112,436

(22) Filed: Apr. 30, 2008

(65) Prior Publication Data

US 2009/0213380 A1 Aug. 27, 2009

Related U.S. Application Data

(60) Provisional application No. 61/030,475, filed on Feb. 21, 2008.

(51) Int. Cl.
*G01N 21/00* (2006.01)

(52) U.S. Cl. ..................................................... 356/437

(58) Field of Classification Search ................. 356/437
See application file for complete search history.

(56) References Cited

U.S. PATENT DOCUMENTS

| | | | |
|---|---|---|---|
| 4,549,080 A | | 10/1985 | Baskins et al. |
| 5,040,895 A | * | 8/1991 | Laurent et al. ............... 356/454 |
| RE34,153 E | * | 12/1992 | Benner et al. ................ 356/301 |
| 5,255,218 A | | 10/1993 | Yagyu et al. |
| 5,451,787 A | | 9/1995 | Taylor |
| 5,570,179 A | * | 10/1996 | Weckstrom .................. 356/311 |
| 5,731,581 A | * | 3/1998 | Fischer et al. ........... 250/339.13 |
| 5,811,812 A | | 9/1998 | Williams et al. |
| 6,218,666 B1 | * | 4/2001 | Lukica et al. ................ 250/343 |
| 6,455,854 B1 | * | 9/2002 | Richman ..................... 250/343 |
| 6,900,893 B2 | * | 5/2005 | Foley et al. .................. 356/437 |
| 6,977,179 B2 | * | 12/2005 | Rue et al. .................... 436/143 |
| 7,132,658 B2 | * | 11/2006 | Weckstrom et al. ..... 250/339.13 |
| 7,400,398 B2 | * | 7/2008 | Stedman ...................... 356/326 |
| 2005/0012042 A1 | * | 1/2005 | Weckstrom et al. ......... 250/343 |
| 2006/0189858 A1 | | 8/2006 | Sterling et al. |
| 2007/0263213 A1 | * | 11/2007 | Stedman ...................... 356/328 |
| 2009/0323068 A1 | * | 12/2009 | Yamakage et al. ........... 356/437 |

OTHER PUBLICATIONS

International Search Report mailed Apr. 29, 2009 in corresponding International Application No. PCT/US2009/34560.

* cited by examiner

*Primary Examiner*—Roy Punnoose
(74) *Attorney, Agent, or Firm*—Chapin IP Law, LLC; Barry W. Chapin, Esq.

(57) ABSTRACT

A gas analyzer system includes an optical source, an optical filter assembly, a controller, and an analyzer. The optical source generates an optical signal. The optical filter assembly includes different optical filters in which to filter the optical signal. During operation, the controller selects sequential application of each of the different optical filters in a path of the optical signal to modulate the optical signal using different frequency bands of optical energy. The modulated optical signal passes through an unknown sample. Based on absorption of the optical signal by the sample gas at different frequencies, the optical analyzer detects which types of multiple different gases are present in the sample.

22 Claims, 20 Drawing Sheets

| SAMPLE DATA 138-1 | | SAMPLE DATA 138-2 | | SAMPLE DATA 138-N | |
|---|---|---|---|---|---|
| FILTER | INTENSITY | FILTER | INTENSITY | FILTER | INTENSITY |
| REF | DATA 11 | REF | DATA 21 | REF | DATA N1 |
| REF | DATA 12 | REF | DATA 22 | REF | DATA N2 |
| FB3 | DATA 13 | FB3 | DATA 23 | FB3 | DATA N3 |
| FB4 | DATA 14 | FB4 | DATA 24 | FB4 | DATA N4 |
| FB5 | DATA 15 | FB5 | DATA 25 | FB5 | DATA N5 |
| FB6 | DATA 16 | FB6 | DATA 26 | FB6 | DATA N6 |
| FB7 | DATA 17 | FB7 | DATA 27 | FB7 | DATA N7 |
| FB8 | DATA 18 | FB8 | DATA 28 | FB8 | DATA N8 |
| FB9 | DATA 19 | FB9 | DATA 29 | FB9 | DATA N9 |
| FB10 | DATA 1A | FB10 | DATA 2A | FB10 | DATA NA |
| FB11 | DATA 1B | FB11 | DATA 2B | FB11 | DATA NB |
| FB12 | DATA 1C | FB12 | DATA 2C | FB12 | DATA NC |
| CYCLE #1 | | CYCLE #2 | | CYCLE #N | |

FIG. 4

Interference and Response Coefficients for Pyroelectric Detector Channels

| Channel | 122-2 | 122-3 | 122-4 | 122-5 | 122-6 | 122-7 | 122-8 | 122-9 | 122-10 | 122-11 | 122-12 | 122-1 |
|---|---|---|---|---|---|---|---|---|---|---|---|---|
| Wavelength in μm | 3.731 | 2.554 | 4.63 | 4.843 | 5.25 | 6.211 | 8.696 | 7.831 | 3.236 | 3.367 | 3.896 | 3.731 |
| Interferent | Ref | H2O | CO | CO2 | NO | NO2 | SO2-L | N2O-L | CH4 | HC | N2O-H | Ref | a' => a'

| Interferent | | 122-2 | 122-3 | 122-4 | 122-5 | 122-6 | 122-7 | 122-8 | 122-9 | 122-10 | 122-11 | 122-12 | 122-1 |
|---|---|---|---|---|---|---|---|---|---|---|---|---|---|
| Ref | C1 | 0 | 0 | 0 | 0 | 0 | 0 | 0 | 0 | 0 | 0 | 0 | 0 |
|  | C2 | 0 | 0 | 0 | 0 | 0 | 0 | 0 | 0 | 0 | 0 | 0 | 0 |
| H2O | C1 | -0.0237 | 0 | 0.0072 | 0 | 0.0984 | 0.4044 | 0 | 0 | 0.0528 | 0.111 | 0.0214 | 0 |
|  | C2 | 0 | 0 | 0 | 0 | 0 | 0 | 0 | 0 | 0 | -0.305 | -0.0026 | 0 |
| CO | C1 | 0 | -0.1174 | 0 | 0.3735 | 0 | -0.016 | -0.0132 | 0 | 0 | 0 | 0 | 0 |
|  | C2 | 0 | 0.0699 | 0 | 0.0467 | 0 | 0.0113 | 0.0122 | 0 | 0 | 0 | 0 | 0 |
| CO2 | C1 | 0 | 0.0231 | 0 | 0 | 0.1256 | 0 | 0 | 0 | 0 | 0 | 0 | 0 |
|  | C2 | 0 | 0 | 0 | 0 | 0.1759 | 0.0708 | 0 | 0 | 0 | 0 | 0 | 0 |
| NO | C1 | 0 | 0 | 1.1018 | -0.0382 | -0.0402 | -0.0611 | 0 | 0.0299 | -0.0053 | -0.0047 | 0 | 0 |
|  | C2 | 0 | 0 | -0.745 | 0 | 0.0169 | 0.0177 | 0 | -0.0073 | 0 | -0.0026 | 0 | 0 |
| NO2 | C1 | 0 | -0.0915 | 0 | 0.0044 | 0 | -0.0107 | 0.0099 | 0 | 0 | -0.0106 | 0 | 0 |
|  | C2 | 0 | 0.0885 | 0 | 0 | 0 | 0 | -0.0417 | 0 | 0.0133 | 0 | 0 | 0 |
| SO2 | C1 | 0 | 0 | 0 | 0 | 0 | 0 | 0.0594 | 0 | 0 | 0 | 0 | 0 |
|  | C2 | 0 | 0 | 0 | 0 | 0 | 0 | 0 | 0 | 0 | 0 | 0 | 0 |
| N2O-L | C1 | 0 | 0 | 0 | 0 | 0 | 0 | 0 | 0 | 0 | 0 | 0 | 0 |
|  | C2 | 0 | 0 | 0 | 0 | 0 | 0 | 0 | 0 | 0 | 0 | 0 | 0 |
| CH4 | C1 | 0 | 0 | 0 | 0 | 0 | 0 | 0 | 0 | 0 | 0 | 0 | 0 |
|  | C2 | 0 | 0 | 0 | 0 | 0 | 0 | 0 | 0 | 0 | 0 | 0 | 0 |
| HC | C1 | 0 | 0 | 0 | 0 | 0 | 0 | 0 | 0 | 0 | 0 | 0 | 0 |
|  | C2 | 0 | 0 | 0 | 0 | 0 | 0 | 0 | 0 | 0 | 0 | 0 | 0 |
| N2O-H | C1 | 0 | 0 | 0 | 0 | 0 | 0 | 0 | 0 | 0 | 0 | 0 | 0 |
|  | C2 | 0 | 0 | 0 | 0 | 0 | 0 | 0 | 0 | 0 | 0 | 0 | 0 |
| Ref | C1 | 0 | 0 | 0 | 0 | 0 | 0 | 0 | 0 | 0 | 0 | 0 | 0 |
|  | C2 | 0 | 0 | 0 | 0 | 0 | 0 | 0 | 0 | 0 | 0 | 0 | 0 | a' => c

| Analyte | | 122-2 | 122-3 | 122-4 | 122-5 | 122-6 | 122-7 | 122-8 | 122-9 | 122-10 | 122-11 | 122-12 | 122-1 |
|---|---|---|---|---|---|---|---|---|---|---|---|---|---|
|  | C1 | 0 | 1680 | 797 | 420722 | 851 | 52 | 941 | 298 | 583 | 146 | 1854 | 0 |
|  | C2 | 0 | 5140 | 2405 | 467269 | 911 | 19 | 77 | -22 | 9400 | 0 | -3439 | 0 |

| Filter # | Gas | Detector | CWN cm^-1 | CWL micron | CWL Tolerance +/- % | CWL Tolerance +/- micron | BW % | FWHM micron | FWHM Tolerance +/- micron |
|---|---|---|---|---|---|---|---|---|---|
| | Size: | 0.260" +/- 0.005" square | | | | | | | |
| | Thickness: | 0.040" +/- 0.005" | | | | | | | |
| | All filters to be 3 cavity low index design except NO2 filter #1 is 2 cavity | | | | | | | | |
| | Blocking for 1.5mm CaF2 | | | | | | | | |
| | Operating temperature is 48 C | | | | | | | | |
| | CWL Tolerance As indicated | | | | | | | | |
| | FWHM Tolerance +/- 15% | | | | | | | | |
| 1 | NO2 | Pyro | 1610 | 6.211 | 0.75 | 0.067 | 2.7 | 0.166 | 0.025 |
| 2 | NO | Both | 1908 | 5.241 | 0.75 | 0.039 | 2.4 | 0.126 | 0.019 |
| 3 | Ref | Both | 2680 | 3.731 | 0.75 | 0.028 | 2.1 | 0.078 | 0.012 |
| 4 | High H2O | Pyro | 1845 | 5.420 | 0.75 | 0.041 | 2.7 | 0.146 | 0.022 |
| 5 | CO | Both | 2160 | 4.630 | 0.75 | 0.035 | 2.3 | 0.106 | 0.016 |
| 6 | CO2 | Both | 2065 | 4.843 | 0.75 | 0.036 | 2.4 | 0.116 | 0.017 |
| 7 | High SO2 | Both | 2510 | 3.984 | 0.75 | 0.030 | 2.1 | 0.084 | 0.013 |
| 8 | Medium SO2 | Pyro | 1150 | 8.696 | 0.75 | 0.065 | 5.6 | 0.487 | 0.073 |
| 9 | N2O | Pyro | 1277 | 7.831 | 0.50 | 0.039 | 3.5 | 0.274 | 0.041 |
| 10 | Low H2O (alt) | Both | 3855 | 2.594 | 0.50 | 0.013 | 2.5 | 0.065 | 0.010 |
| 11 | N2O (alt) | Both | 2567 | 3.896 | 0.50 | 0.019 | 1.5 | 0.058 | 0.009 |
| 12 | NO2 SW | Lead | 2895 | 3.454 | 0.50 | 0.017 | 1.5 | 0.052 | 0.008 |
| 13 | CH4 | Both | 3090 | 3.236 | 0.50 | 0.016 | 1.5 | 0.049 | 0.007 |
| 14 | HC | Both | 2970 | 3.367 | 0.50 | 0.017 | 2.0 | 0.067 | 0.010 |
| 15 | CO | Both | 2150 | 4.651 | 0.50 | 0.023 | 2.3 | 0.107 | 0.016 |

GAS ANALYZER SYSTEM

RELATED APPLICATION

This application claims priority to United States Provisional patent application entitled "FLUID ANALYZER SYSTEM" having assigned Ser. No. 61/030,475, filed on Feb. 21, 2008, the entire teachings of which are incorporated herein by this reference.

This application is related to U.S. patent application Ser. No. 12/112,401 entitled "ANALYZER SYSTEM AND OPTICAL FILTERING" filed on the same day as the present application, the entire teachings of which are incorporated herein by this reference.

BACKGROUND

Emissions from fossil fuel combustion facilities, such as flue gases of coal-fired utilities and municipal solid waste incinerators, typically include multiple types of gases. For example, emissions from a smokestack can include gases such as $CO_2$, $NO_2$, $SO_2$, etc.

Many countries regulate emissions of the different types of waste gases because of potential environmental hazards posed by such harmful emissions. Accordingly, many facilities that generate or potentially generate harmful gas emissions need to employ multiple gas analyzer systems to ensure that emitted gas concentrations are compliant with corresponding regulations.

To detect the presence of the many types of gases, a facility may need to operate multiple independent conventional gas analyzer systems and/or measurement benches. For example, a facility may need to operate a first gas analyzer system to detect a first type of gas, a second analyzer system to detect a second type of gas, and so on. Such instruments may combine multiple complex analytical technologies including Electrochemical cells, Chemi-luminescence Spectroscopy, Flame Ionization, GFC (Gas Filter Correlation), NDIR (Non-Dispersive Infrared), or UV (Ultra-Violet) Spectroscopy, etc., into a single gas analyzer unit to detect one or more types of gases.

Each of the different types of gases emitted by a smokestack has unique light absorption characteristics. For example, each gas type can absorb different optical frequencies. The unique absorption characteristics enable a corresponding gas analyzer system to identify whether a particular type of gas is present in a gas sample.

A facility may need to operate multiple independent conventional gas analyzer systems and/or measurement benches to detect a presence of multiple gases of interest. Each conventional gas analyzer system typically requires its own set of operating procedures, calibration procedures, etc. to collect accurate data.

One way to identify a type of gas present in an unknown gas sample is the application of Beer's law. In general, Beer's law defines a relationship that relates the absorption of light to properties of the material through which the light is traveling. In other words, as mentioned above, different materials absorb different frequencies of light energy. Based on the passage of optical energy through a gas sample and subsequent detection of the frequencies of optical energy that are absorbed by the gas sample, it is possible to determine what type of gas is present in the gas sample. For example, the amount of absorption by a sample can indicate the concentration of a respective gas.

A conventional gas analyzer system includes an optical source that generates an optical signal for passing through a sample gas. Such a conventional analyzer can include a so-called optical filter wheel and a so-called chopper wheel. The optical filter wheel and the chopper are both disposed in the path of the optical signal.

The optical filter wheel can include a number of different optical filters, each of which passes only a single, narrow frequency band of optical energy. Depending on which filter is disposed in the path of the optical signal, it is known what frequency band of light is being passed through the sample. An optical detector measures how much optical energy passes though the sample.

The chopper wheel includes multiple windows or cut-outs separated by opaque regions that block light. As mentioned, the chopper wheel is also placed in the path of the optical signal such that a position of the chopper wheel dictates whether any of the optical energy passes through the gas sample or is blocked by an opaque region. As the chopper wheel spins, it blocks and passes optical energy of a particular frequency band through the sample to a detector.

During operation, a conventional gas analyzer system produces modulated light by setting the filter wheel in a position so that the optical signal passes through a selected filter in the optical wheel. When the selected filter is in such a position, a controller spins the chopper wheel to repeatedly block and pass the optical signal through the gas sample as discussed above. Application of the chopper wheel results in the modulation of a single frequency band of optical energy depending on which filter on the filter wheel has been chosen to be "chopped" or modulated. Accordingly, a controller can produce a modulated optical signal using a two-wheel assembly including a chopper wheel and filter wheel.

SUMMARY

As a result of increasing industrialization and concern over the world-wide impact of air pollution, there is an increasing need for continuous emissions monitoring systems (CEMS) that can be installed at emissions sources such as power plants and incinerators.

Conventional methods of analyzing and detecting the presence of multiple different types of gases in a sample suffer from a number of deficiencies. For example, as mentioned above, a facility may need to operate multiple independent conventional gas analyzer systems and/or measurement benches to detect the presence of multiple gases present in sample flue gas. Each conventional gas analyzer system typically requires its own set of operating procedures, calibration procedures, etc. to produce and collect accurate data for different types of gases of interest.

In certain cases, a conventional "multi-gas" analyzer system is capable of measuring more than one gas component. Such instruments typically combine multiple analytical technologies including Electrochemical Cells, Chemi-Luminescence Spectroscopy, Flame Ionization, GFC (Gas Filter Correlation), NDIR (Non-Dispersive Infrared) and UV (Ultra-Violet) Spectroscopy into a single gas analyzer unit. While many of these systems are currently in-use, they suffer limitations in the areas of cost, reliability, maintenance and performance.

Embodiments herein include a unique and useful system configured to detect the presence of different types of gases. For example, certain embodiments herein include a multi-component analyzer that utilizes a single analytical bench to measure a multiplicity of pollutants, including, but not necessarily limited to NO, $NO_2$, CO, $CO_2$, $SO_2$, HF, HCl, $N_2O$, hydrocarbons, etc.

More specifically, an example system herein includes an optical source, a detector, and an analyzer. The optical source generates an optical signal. The detector measures an intensity of the optical signal after passage of the optical signal through a sample gas. When present, different gases in the sample gas absorb optical energy in the same and/or different frequency bands. The analyzer utilizes absorption data collected by the detector to calculate which of multiple types of gases are present in the sample gas.

It is possible that two or more of the different gases present in the sample absorb optical energy in a common frequency band of the modulated optical signal due to absorbance interference. This complicates the task of detecting which types of gases may be present in the sample. Thus, merely knowing that a gas sample absorbs a given frequency or frequency band of light energy may not be enough information to determine which specific type of gas is present in the sample.

To discern between different gases, the analyzer measures absorption of optical energy in a number of frequency bands where one or more gases are expected to absorb optical energy. Depending on how much energy is absorbed in different optical frequency bands, the gas analyzer system according to embodiments herein can identify concentrations of different types of gases in a sample even though there happens to be absorbance interference amongst one or more of the gases in the same frequency bands.

For example, assume that two or more gases in the sample gas may absorb optical energy in the same frequency band. To account for such absorbance interference at the same frequency band, the analyzer measures absorbance of the optical signal by the sample gas at different optical frequency bands. Based on absorbance measurements at the different frequency bands, the analyzer is able to account for absorbance interference and detect concentrations of the multiple types of gases present in the sample.

In one embodiment, measuring absorption of the optical signal includes implementing a sequence of measuring absorbance of the sample gas at different frequency bands. The measuring sequence can include taking an absorbance measurement of the optical signal at a first frequency band followed by taking an absorbance measurement of the optical signal at a second frequency band followed by taking an absorbance measurement of the optical signal at a third frequency, and so on. In one embodiment, the analyzer initiates cyclical application of the sequence to repeatedly measure absorbance of the sample gas at the different frequency bands in a serial manner.

By way of a non-limiting example, the analyzer can implement the sequence of measurements as mentioned above by initiating rotation of an optical filter wheel assembly to align filters of the optical filter assembly in the path of the optical signal to filter the optical signal at the different frequency bands. Rotation of the optical filter assembly can include spinning the optical filter wheel and aligning a first filter of the optical filter assembly in the path of the optical signal to measure absorbance by the sample gas at the first frequency band, followed by aligning a second filter of the optical filter assembly in the path of the optical signal to measure absorbance by the sample gas at the second frequency band, followed by aligning a third filter of the optical filter assembly in the path of the optical signal to measure absorbance by the sample gas at the third frequency band, and so on.

Note that in one embodiment, rotation of the optical filter wheel in this manner produces the optical signal as a modulated optical signal for passing through the sample gas.

To detect the concentrations of multiple types of gases in the sample gas, the analyzer utilizes absorbance measurements of the optical signal in multiple frequency bands such as absorbance measurements at a first frequency band and a second frequency band to calculate a concentration of a first gas present in the sample gas. The analyzer can also utilize absorbance measurements of the optical signal at the first frequency band and the second frequency band to calculate a concentration of a second gas present in the sample gas.

In one embodiment, the analyzer utilizes the different frequency bands to detect a concentration of the different types of gases. For example, the analyzer uses absorption measurements in a first frequency band to detect a concentration of a first gas type in the sample gas. The analyzer uses absorption measurements in a second frequency band of the multiple frequency bands to detect a concentration of a second gas type in the sample gas.

In yet further embodiments, the analyzer can be configured to repeatedly measure absorbance of the optical signal by the sample gas at the multiple frequency bands over multiple absorbance measurement collection cycles. For example, the analyzer repeats a sequence of collecting absorbance measurement data over multiple collection cycles. Based on the absorbance measurements in different frequency bands over multiple cycles, the analyzer detects the concentrations of the multiple types of gases in the sample gas via successive approximations.

More specifically, in one embodiment, the analyzer measures absorbance of the optical signal by the sample gas at the first frequency band and the second frequency band in a first measurement cycle. Subsequent to the first measurement cycle, the analyzer measures absorbance of the optical signal by the sample gas at the first frequency band and the second frequency band in a second measurement cycle.

The analyzer calculates a concentration of the first gas type in the sample gas based at least in part on an absorbance measurement obtained in the second cycle for the first frequency band and an absorbance measurement in the first cycle for the second frequency band. The analyzer calculates a concentration of the second gas type in the sample gas based at least in part on an absorbance measurement obtained in the second cycle for the second frequency band and an absorbance measurement in the first cycle for the first frequency band.

Techniques herein are well suited for use in applications such as those supporting detection of different types of gases in an unknown gas sample. However, it should be noted that configurations herein are not limited to such use and thus configurations herein and deviations thereof are well suited for use in other environments as well.

Note that each of the different features, techniques, configurations, etc. discussed herein can be executed independently or in combination. Accordingly, the present invention can be embodied and viewed in many different ways.

Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details and/or possible perspectives or permutations of the invention, the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein as illustrated in the accompanying drawings in which like reference characters refer to the same parts throughout the different views. The drawings are not necessarily to scale, with emphasis instead being placed upon illustrating the embodiments, principles and concepts.

FIG. 4 is an example diagram illustrating collected sample data according to embodiments herein.

FIG. 13 is a table illustrating example coefficient values for implementing interference correction according to embodiments herein.

FIG. 18 is an example table illustrating different filters for use in a sample gas analyzer according to embodiments herein.

DETAILED DESCRIPTION

Figure 1:
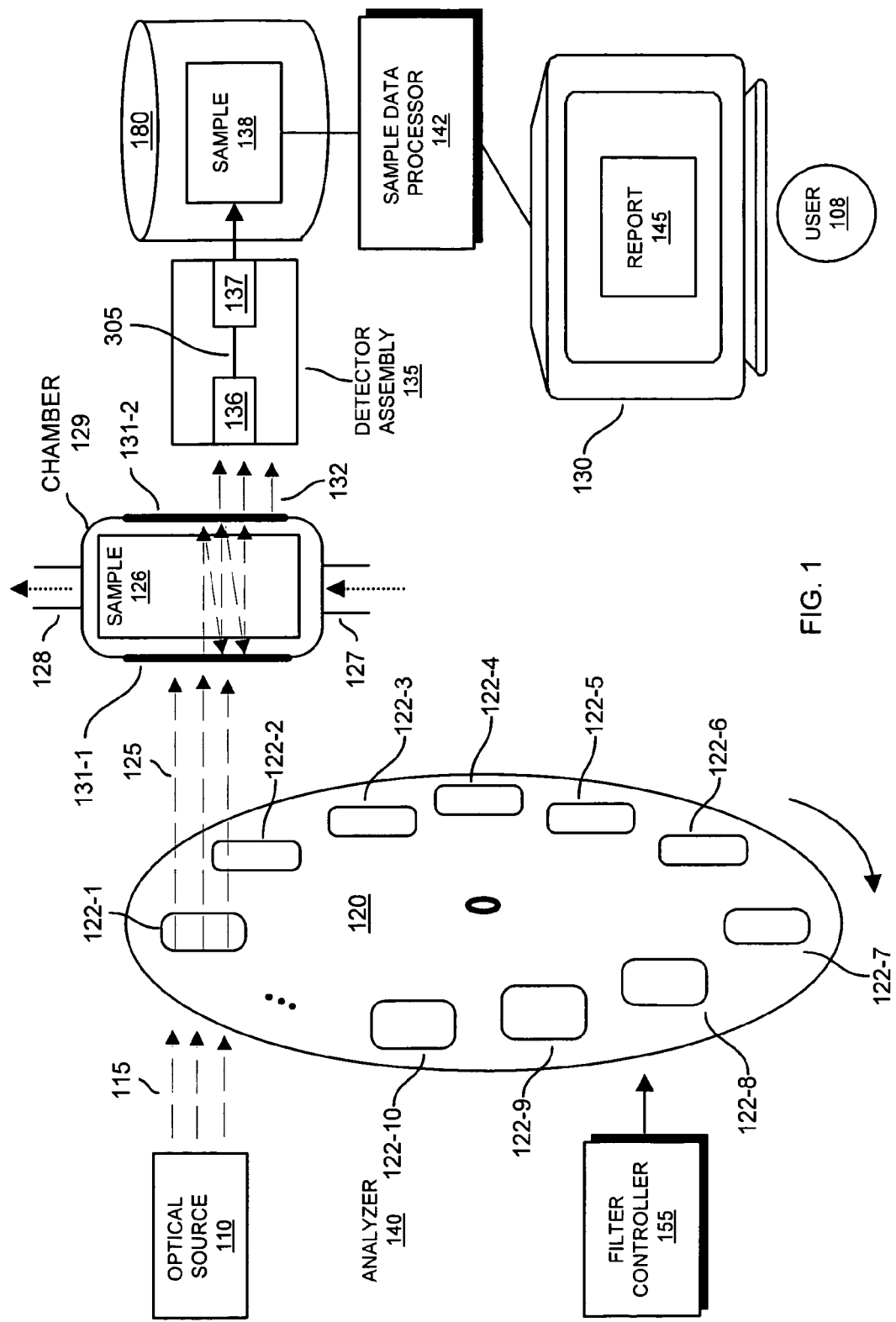
FIG. 1 is an example diagram of an analyzer system according to embodiments herein.

Now, more specifically, FIG. 1 is an example diagram of an analyzer system 100 according to embodiments herein. As shown, analyzer system 100 includes a user 108, an optical source 110, optical signal 115, optical filter assembly 120, modulated optical signal 125, chamber 129, detector assembly 135, repository 180, sample data processor 142, and display screen 130. Optical filter assembly 120 includes multiple filters 122 such as filter 122-1, filter 122-2, filter 122-3, filter 122-4, filter 122-5, filter 122-6, filter 122-7, filter 122-8, filter 122-9, filter 122-10, etc. Chamber 129 includes inlet 127, outlet 128, and reflectors 131-1 and 131-2. Display screen 130 displays report 145 for viewing by user 108. Detector assembly 135 includes detector 136 and monitor circuit 137.

In general, analyzer system 100 analyzes absorption characteristics of sample 126 as it passes from inlet 127 through chamber 129 to outlet 128. The analyzer system 100 passes the modulated optical signal 125 through the sample 126 to identify a presence and/or concentrations of multiple different target gases such as $H_2O$ (water), CO (carbon monoxide), $CO_2$ (carbon dioxide), NO (nitric oxide), $NO_2$ (nitrogen dioxide), $SO_2$ (sulfur dioxide), $N_2O$ (nitrous oxide), $CH_4$ (methane), HC (hydrocarbons), etc.

By way of a non-limiting example, the inlet 127 of chamber 128 can be configured to receive gas sample 126 from a smokestack. In such an embodiment, the analyzer system 100 measures combustion by-products in sample 126 using a unique method employing non-dispersive infrared (NDIR) absorbance spectroscopy.

The basis of analyzing sample 126 according to one embodiment is the use of Beer-Lambert's Law. As mentioned above, this law defines a relationship between the concentration of a gas of interest and the amount of energy it absorbs. Via this technique, the gas analyzer 140 determines the presence and/or concentration of matter such as individual pollutants in the sample 126 based on the capacity of the compounds to absorb infrared energy of a specific wavelength.

During operation, optical source 110 generates optical signal 115. In one embodiment, and by way on a non-limiting example, the optical source generates optical signal 115 in an infrared spectrum such as a broad range of optical wavelengths between 1.5 and 9.5 micrometers. The optical source 115 can be a device such as semiconductor device, a glowing metal filament heated to a temperature of several hundred degrees C., etc.

In one embodiment, the optical detector 136 is a pyroelectric detector device such as the Selex detector Type #5482 (SELEX S&AS, PO Box 217, Millbrook Industrial Estate, Southampton, Hampshire, UK).

In accordance with another embodiment, the detector device is a lead-selenide device such as the SensArray detector, part number SA-432-386T (available from SensArray Infrared, Burlington, Mass. 01803).

As its name suggests, filter controller 155 changes which of the multiple optical filters 122 is aligned in the path of the optical signal 115 for passage of a limited frequency band of the optical signal 115 through sample 126 to detector 136. The filter controller 155 produces the modulated optical signal 125 by rotating an optical filter assembly 120 to each of multiple successive positions in which the optical filters 122 pass different frequency bands of optical energy through the sample 126.

As an example, optical filter assembly 120 can be a filter wheel that spins in response to input by the filter controller 155.

More specifically, the filter controller 155 rotates optical filter assembly 120 so that optical filter 122-1 of the optical filter assembly 120 initially lies in the path of the optical signal 115. When in such a position, the filter 122-1 absorbs certain frequencies in the optical signal 115 and passes other frequencies of the optical signal 115 to sample 126 in chamber 129.

As the optical filter assembly 120 rotates further, filter 122-1 moves out of the path of optical signal 115. The opaque partition of the optical filter assembly 120 between filter 122-1 and filter 122-2 then temporarily blocks the optical signal 115 so that substantially little or no optical energy passes through the sample 126 in chamber 129 to detector 126.

The filter controller 155 continues to rotate optical filter assembly 120 so that optical filter 122-2 aligns in the path of the optical signal 115. When in such a position, the filter 122-2 absorbs certain frequencies in the optical signal 115 and passes other frequencies of the optical signal 115 to sample 126 in chamber 129.

As the optical filter assembly 120 rotates further, filter 122-2 moves out of the path of optical signal 115. The opaque partition of the optical filter assembly 120 between filter 122-2 and filter 122-3 then temporarily blocks the optical signal 115 so that substantially little or no optical energy passes through the sample 126 in chamber 129.

The filter controller 155 continues to rotate optical filter assembly 120 so that optical filter 122-3 of the optical filter assembly 120 lies in the path of the optical signal 115. When in such a position, the filter 122-3 absorbs certain frequencies in the optical signal 115 and passes other frequencies of the optical signal 115 to sample 126 in chamber 129.

Based on repeating the above sequence of blocking and filtering different portions of the optical signal 115 over time, analyzer system 100 produces the modulated optical signal 125 by multiplexing different frequency bands of the optical signal 115 through the sample. Each filter 122 can pass one or more frequency bands or channels of optical energy to the optical detector 136.

As mentioned above, the analyzer system 100 passes the (multi-frequency) modulated optical signal 125 through sample 126. Depending on how much energy in the different energy bands is absorbed by the sample, the analyzer 140 detects types of gas present in the chamber 126 as well as a concentration of the detected gases.

By way of a non-limiting example, the filter controller 155 can initiate spinning of the optical filter assembly 120 at a rate such as thirty rotations per second. In such an embodiment, assuming there are twelve filters on the optical filter assembly 120, the detector 136 and sampling circuit 137 collects three hundred sixty intensity samples or thirty samples per each filter for each second.

The rate of rotating the optical filter assembly 120 to collect data can vary depending on such factors as how many filters are present in the optical filter assembly 120, the ability of the detector 136 to take a reading, etc.

The chamber 129 can include reflector 131-1 and reflector 131-2 to increase the optical path length of the modulated optical signal 125 as it passes through the sample 126. Increasing the effective optical path length of the modulated optical signal 125 in the chamber 129 enables greater absorption of the modulated optical signal 125 when a target gas happens to be present in the chamber 129. This results in more accurate gas type determinations, greater sensitivity, and/or more accurate gas concentration readings.

After passing through chamber 129, the portion of the modulated optical signal 132 that is not absorbed by the sample 126 strikes detector assembly 136. By way of a non-limiting example, an output signal 305 such as an output voltage of the detector 136 varies depending on how much energy is present in the optical signal 132. Monitor circuit 137 can include an amplifier and A/D circuit (e.g., analog to digital converter circuit) to measure the strength of the received optical signal 132. For example, the monitor circuit 137 samples the intensity of the detector 136 to produce sample data 138. For example, detector assembly 135 then stores intensity readings associated with optical signal 132 as sample data 138 in repository 180.

By way of a non-limiting example, an output signal 305 such as an output voltage of the detector 136 varies depending on how much energy is present in the optical signal 132. Monitor circuit 137 can include an amplifier and A/D circuit (e.g., analog to digital converter circuit) to measure the strength of the received optical signal 132.

Figure 3:
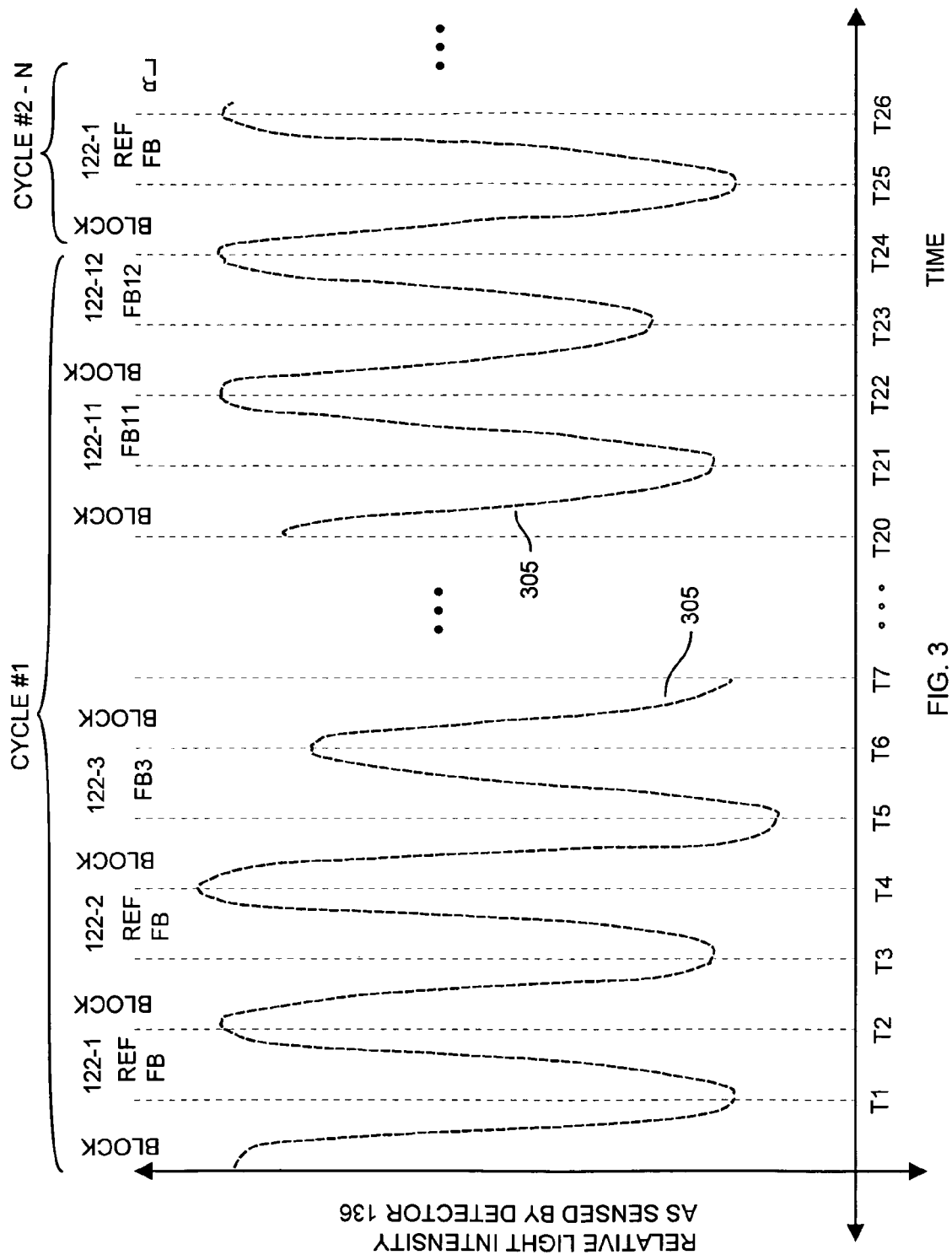
FIG. 3 is an example diagram illustrating detected intensities of light for different frequency bands according to embodiments herein.

In an example embodiment, the detector assembly 135 can be configured to detect peak values and trough values associated with the optical signal 132 as illustrated in FIG. 3. As will be discussed later in this specification, peaks and troughs provide a relative measure of how much of the optical energy at the different frequency bands has been absorbed by the sample 126.

The sample data processor 142 of analyzer 140 processes the sample data 138 such as peak and trough information at the different frequency bands to identify which, if any, types of gases are present in the chamber 129 as well as concentrations of these gases. Via report 145 on display screen 130, the analyzer 140 can indicate the different types of gases and concentrations in the sample 126 for viewing by user 108.

A benefit of sequentially collecting data in the different frequency bands is the ability to more accurately detect a presence of fast moving gases in chamber 126. For example, conventional methods include setting a filter in a path of an optical signal and chopping the frequency with a so-called chopper wheel as discussed above. In such an embodiment, a fast moving gas of a particular type may not be detected because the conventional analyzer did not sample the appropriate frequency bands while the fast passing gas was present in a sample chamber. Embodiments herein include sequentially collecting data from different frequency bands. In such embodiments, a fast passing gas in the chamber 129 is more likely to be detected by the analyzer 140 because the frequency bands are changed more frequently.

Figure 2:
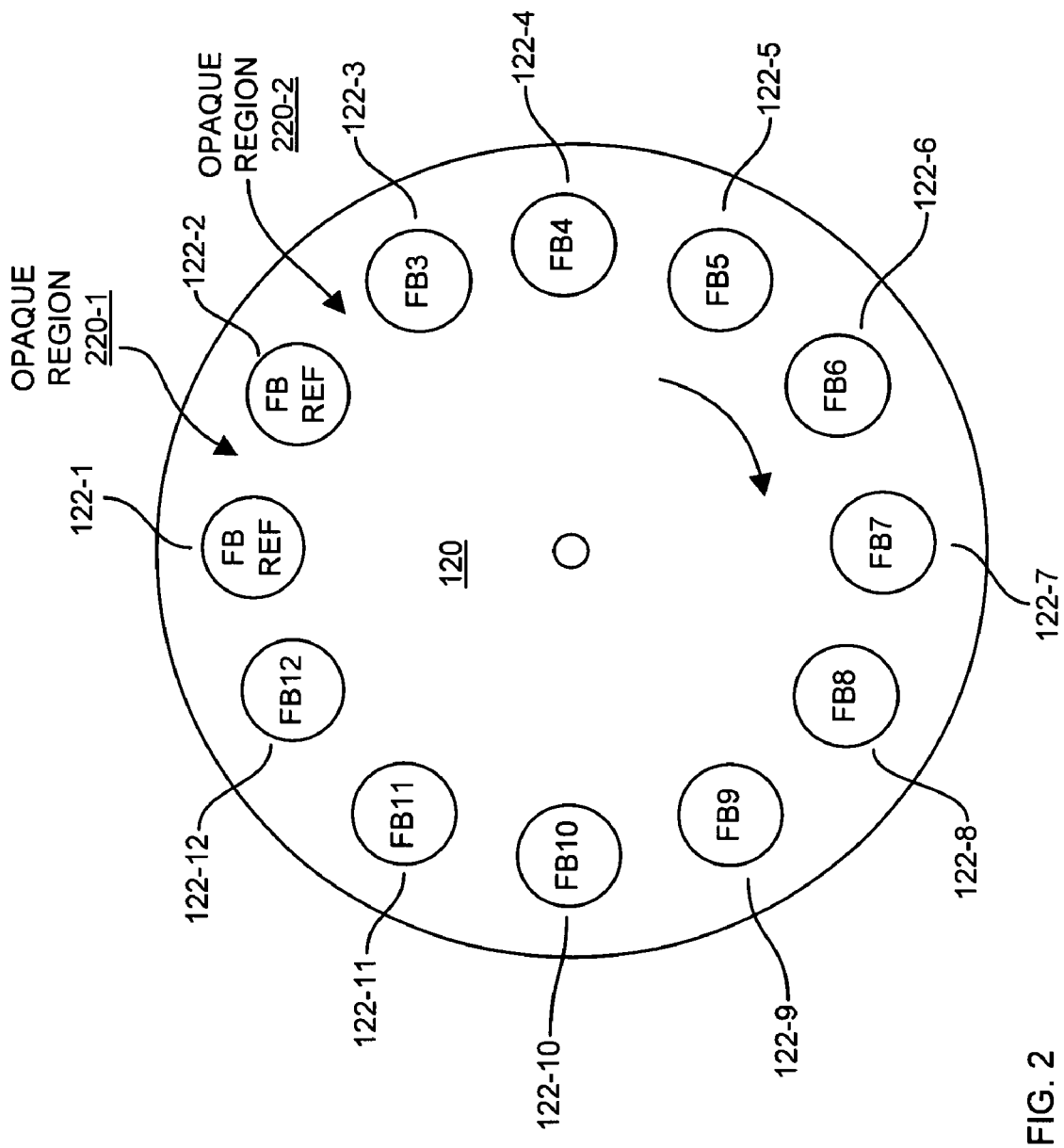
FIG. 2 is an example diagram illustrating an optical filter assembly according to embodiments herein.

FIG. 2 is a diagram illustrating an example filter assembly 120 for filtering optical signal 115 and producing modulated optical signal 125 according to embodiments herein. As shown, optical filter assembly 120 includes multiple filters 122 including reference filter 122-1, reference filter 122-2, filter 122-3, filter 122-4, filter 122-5, filter 122-6, filter 122-7, filter 122-8, filter 122-9, filter 122-10, filter 122-11, and filter 122-12. Opaque regions 220 such as opaque region 220-1, opaque region 220-2, opaque region 220-3, and so on, block optical energy from passing through sample 126.

Note that use of twelve filters is shown by way of example only and that optical filter assembly 120 can include any practical number of filters.

Each of the filters 122 can be chosen so that it is possible for the analyzer 140 to identify which, if any, types of the target type gases are present in the sample 126 passing through the chamber 129. As previously discussed, the target gases can include gases such as $H_2O$ (water), CO (carbon monoxide), $CO_2$ (carbon dioxide), NO (nitric oxide), $NO_2$ (nitrogen dioxide), $SO_2$ (sulfur dioxide), $N_2O$ (nitrous oxide), $CH_4$ (methane), HC (hydrocarbons), etc.

By way of a non-limiting example, the filters 122 can be configured as follows:

Each of reference filter 122-1 and reference filter 122-2 can be configured to have a center wavelength of approximately 3.731 micrometers+/−2 percent. The filter 122-1 can have a FWHM (Full Width at Half Maximum) of 0.08 micrometers+/−15 percent and CWN (Center Wave Number) of around 2680 $cm^{-1}$+/−1 percent. Of course, these are examples only and the actual filters can vary depending on a respective application.

Assuming that the center wavelength of filter 122-1 is 3.731 micrometers, when the filter 122-1 is positioned in a path of the optical signal 115, the filter 122-1 passes a wavelength band or range of energy centered around 3.731 micrometers.

In one embodiment, the center frequency value of filter 122-1 such as 3.731 micrometers is chosen such that the filter passes a range of energy wavelengths that are not absorbed by any of the target gases. Use of such reference channels (i.e., filter 122-1 and filter 122-2) serve as a way to correct for drift associated with other channels in the analyzer system 100. Drift can be caused by factors such as changes in the intensity of the optical signal 115 produced by 115 over time, changes in the detector and its ability to detect optical signal 132 over time, etc. If used for correction of drift, the readings produced by the analyzer system 100 typically will be more accurate.

Disposing of the reference filters 122-1 and 122-2, one after the other in a sampling sequence, enables the analyzer system 100 to obtain a more accurate reference reading because the first reference filter 122-1 establishes a good pre-sample for taking a following reading with filter 122-2.

Filter 122-3 can be configured to have a center wavelength of approximately 2.594 micrometers+/−2 percent. The filter 122-2 can also have a FWHM (Full Width at Half Maximum) of 0.07 micrometers+/−15 percent and CWN (Center Wave Number) of around 3855 $cm^{-1}$+/−1 percent.

Assuming that the center wavelength of filter 122-3 is 2.594 micrometers, when the filter 122-3 is positioned in a path of the optical signal 115, the filter 122-3 passes a wavelength band or range of energy centered around 2.594 micrometers. This frequency band is at least partially absorbed by $H_2O$ (water) when present in the sample 126. Other gases that absorb energy in this range, and which are possibly present in sample 126, include: CO (carbon monoxide), $CO_2$ (carbon dioxide), and $N_2O$ (nitrous oxide).

Filter 122-4 can be configured to have a center wavelength of approximately 4.630 micrometers+/−2 percent. The filter 122-4 can also have a FWHM (Full Width at Half Maximum) of 0.1 micrometers+/−15 percent and CWN (Center Wave Number) of around 2160 $cm^{-1}$+/−1 percent.

Assuming that the center wavelength of filter 122-4 is 4.630 micrometers, when the filter 122-4 is positioned in a path of the optical signal 115, the filter 122-4 passes a wavelength band or range of energy centered around 4.630 micrometers. This frequency band is at least partially absorbed by CO (carbon monoxide) when present in the sample 126. Other gases that absorb energy in this range, and which are possibly present in sample 126, include: $H_2O$ (water) and $N_2O$ (nitrous oxide).

Filter 122-5 can be configured to have a center wavelength of approximately 4.843 micrometers+/−2 percent. The filter 122-5 can also have a FWHM (Full Width at Half Maximum) of 0.1 micrometers+/−15 percent and CWN (Center Wave Number) of around 2065 $cm^{-1}$+/−1 percent.

Assuming that the center wavelength of filter 122-5 is 4.843 micrometers, when the filter 122-5 is positioned in a path of the optical signal 115, the filter 122-5 passes a wavelength band or range of energy centered around 4.843 micrometers. This frequency band is at least partially absorbed by $CO_2$ (carbon dioxide) when present in the sample 126. Other gases that absorb energy in this range, and which are possibly present in sample 126, include: CO (carbon monoxide), NO (nitric oxide), and SO2 (sulfur dioxide).

Filter 122-6 can be configured to have a center wavelength of approximately 5.25 micrometers+/−2 percent. The filter 122-6 can also have a FWHM (Full Width at Half Maximum) of 0.1 micrometers+/−15 percent and CWN (Center Wave Number) of around 1908 $cm^{-1}$+/−1 percent.

Assuming that the center wavelength of filter 122-6 is 5.25 micrometers, when the filter 122-6 is positioned in a path of the optical signal 115, the filter 122-6 passes a wavelength band or range of energy centered around 5.25 micrometers. This frequency band is at least partially absorbed by NO (nitric oxide) when present in the sample 126. Other gases that absorb energy in this range, and which are possibly present in sample 126, include: $H_2O$ (water), $CO_2$ (carbon dioxide), and $NO_2$ (nitrogen dioxide).

Filter 122-7 can be configured to have a center wavelength of approximately 6.211 micrometers+/−2 percent. The filter 122-7 can also have a FWHM (Full Width at Half Maximum) of 0.2 micrometers+/−15 percent and CWN (Center Wave Number) of around 1610 $cm^{-1}$+/−1 percent.

Assuming that the center wavelength of filter 122-7 is 6.211 micrometers, when the filter 122-7 is positioned in a path of the optical signal 115, the filter 122-7 passes a wavelength band or range of energy centered around 6.211 micrometers. This frequency band is at least partially absorbed by $NO_2$ (nitrogen dioxide) when present in the sample 126. Other gases that absorb energy in this range, and which are possibly present in sample 126, include: $H_2O$ (water), CO (carbon monoxide), NO (nitric oxide), $SO_2$ (sulfur dioxide), and $N_2O$ (nitrous oxide).

Filter 122-8 can be configured to have a center wavelength of approximately 8.696 micrometers+/−2 percent. The filter 122-8 can also have a FWHM (Full Width at Half Maximum) of 0.5 micrometers+/−15 percent and CWN (Center Wave Number) of around 1150 $cm^{-1}$+/−1 percent.

Assuming that the center wavelength of filter 122-8 is 8.696 micrometers, when the filter 122-8 is positioned in a path of the optical signal 115, the filter 122-8 passes a wavelength band or range of energy centered around 8.696 micrometers. This frequency band is at least partially absorbed by $SO_2$ (sulfur dioxide) when present in the sample 126. Other gases that absorb energy in this range, and which are possibly present in sample 126, include: CO (carbon monoxide), $NO_2$ (nitrogen dioxide), and $N_2O$ (nitrous oxide).

Filter 122-9 can be configured to have a center wavelength of approximately 7.831 micrometers+/−2 percent. The filter 122-9 can also have a FWHM (Full Width at Half Maximum) of 0.3 micrometers+/−15 percent and CWN (Center Wave Number) of around 1277 $cm^{-1}$+/−1 percent.

Assuming that the center wavelength of filter 122-9 is 7.831 micrometers, when the filter 122-9 is positioned in a path of the optical signal 115, the filter 122-9 passes a wavelength band or range of energy centered around 7.831 micrometers. This frequency band is at least partially absorbed by $N_2O$ (nitrous oxide) when present in the sample 126. Other gases that absorb energy in this range, and which are possibly present in sample 126, include: $SO_2$ (sulfur dioxide).

Filter 122-10 can be configured to have a center wavelength of approximately 3.236 micrometers+/−2 percent. The filter 122-10 can also have a FWHM (Full Width at Half Maximum) of 0.05 micrometers+/−15 percent and CWN (Center Wave Number) of around 3090 $cm^{-1}$+/−1 percent.

Assuming that the center wavelength of filter 122-10 is 3.236 micrometers, when the filter 122-10 is positioned in a path of the optical signal 115, the filter 122-10 passes a wavelength band or range of energy centered around 3.236 micrometers. This frequency band is at least partially absorbed by $CH_4$ (methane) when present in the sample 126. Other gases that absorb energy in this range, and which are possibly present in sample 126, include: $H_2O$ (water), $SO_2$ (sulfur dioxide), and $N_2O$ (nitrous oxide).

Filter 122-11 can be configured to have a center wavelength of approximately 3.367 micrometers+/−2 percent. The filter 122-11 can also have a FWHM (Full Width at Half Maximum) of 0.1 micrometers+/−15 percent of the center wavelength and CWN (Center Wave Number) of around 2970 $cm^{-1}$+/−1 percent.

Assuming that the center wavelength of filter 122-11 is 3.367 micrometers, when the filter 122-11 is positioned in a path of the optical signal 115, the filter 122-11 passes a wavelength band or range of energy centered around 3.367 micrometers. This frequency band is at least partially absorbed by HC (hydrocarbons) when present in the sample 126. Other gases that absorb energy in this range, and which are possibly present in sample 126, include: $H_2O$ (water), $NO_2$ (nitrogen dioxide), $SO_2$ (sulfur dioxide), and $N_2O$ (nitrous oxide).

Filter 122-12 can be configured to have a center wavelength of approximately 3.896 micrometers+/−2 percent. The filter 122-12 can also have a FWHM (Full Width at Half Maximum) of 0.1 micrometers+/−15 percent of the center wavelength and CWN (Center Wave Number) of around 2567 $cm^{-1}$+/−1 percent.

Assuming that the center wavelength of filter 122-12 is 3.896 micrometers, when the filter 122-12 is positioned in a path of the optical signal 115, the filter 122-12 passes a wavelength band or range of energy centered around 3.896 micrometers. This frequency band is at least partially absorbed by $N_2O$ when present in the sample 126. Other gases that absorb energy in this range, and which are possibly present in sample 126, include: $H_2O$ (water), $NO_2$ (nitrogen dioxide) and $SO_2$ (sulfur dioxide).

Note again that the center frequencies and frequency bands as discussed above for each of the filters 122 is presented as an example only and that these values can vary depending on the embodiment or which types of gases are to be detected in sample 126 passing through chamber 129. Generally, filters 122 can be any values that allow passage of bands of optical energy that can be absorbed by sample 126 and aid in discerning which of multiple gases are present in the sample 126.

As will be discussed later in this specification, each of filters 122-3 through 122-12 in the above example can be assigned or allocated for detecting a particular gas type potentially in sample 126. For example, the frequency band of filter 122-3 can be used to detect $H_2O$ when present in the sample 126, filter 122-4 can be used to detect CO when present in the sample 126, filter 122-5 can be used to detect $CO_2$ when present in the sample 126, filter 122-6 can be used to detect NO when present in the sample 126, filter 122-7 can be used to detect $NO_2$ when present in the sample 126, filter 122-8 can be used to detect $SO_2$ when present in the sample 126, filter 122-9 can be used to detect $N_2O$ when present in the sample 126, filter 122-10 can be used to detect $CH_4$ when present in the sample 126, filter 122-11 can be used to detect HC when present in the sample 126, filter 122-12 can be used to detect $N_2O$ when present in the sample 126, and so on. Recall again that filters 122-1 and 122-2 are used as reference filters.

Thus, embodiments herein can include allocating each of multiple different filter frequency bands to detect a particular concentration of a gas type potentially in a gas 126. In other words, as discussed above, the analyzer 140 can allocate use of frequency band based on filter 122-3 to detect a concentration of $H_2O$ when present in the sample 126, filter 122-4 can be allocated to detect CO when present in the sample 126, filter 122-5 can be allocated to detect $CO_2$ when present in the sample 126, etc.

FIG. 3 is an example diagram illustrating intensities of optical energy for different frequency bands according to embodiments herein. As shown, detector 136 senses a magnitude of light energy in a respective frequency band depending on which filter is in the path of optical signal 115. Signal 305 such as an output voltage of the detector 136 represents a measure of how much optical energy is detected by detector 136. As previously discussed, sample 126 absorbs a certain portion of optical energy passed by a respective filter depending on which of one or more types of gases are present in sample 126.

Between time T0 and time T1, the light-blocking region of optical filter assembly 120 between filter 122-12 and filter 122-1 passes the path of optical signal 115. Because the signal is being blocked during such time, the intensity of signal 305 decreases.

Between time T1 and time T2, the reference filter 122-1 passes the path of optical signal 115. Because a respective frequency band of optical signal 115 passes though filter 122-1 during such time, the intensity of signal 305 increases. As previously discussed, the amount of optical energy detected by detector 136 will vary depending on how much of the optical signal is absorbed by sample 126.

Between time T2 and time T3, the light-blocking region or opaque region of optical filter assembly 120 between filter 122-1 and filter 122-2 passes the path associated with optical signal 115. Because the optical signal 115 is being blocked during such time, the intensity of signal 305 decreases.

Between time T3 and time T4, the reference filter 122-2 passes the path of optical signal 115. Because a respective frequency band of optical signal 115 passes though filter 122-2 during such time, the intensity of signal 305 increases.

Between time T4 and time T5, the light-blocking region or opaque region of optical filter assembly 120 between filter 122-2 and filter 122-3 passes the path of optical signal 115. Because the optical signal 115 is blocked during such time, the intensity of signal 305 decreases.

Between time T5 and time T6, the $H_2O$ (water) filter 122-3 passes the path of optical signal 115. Because a respective frequency band of optical signal 115 passes though filter 122-2 during such time, the intensity of signal 305 increases.

Eventually, the analyzer 140 repeats the same sequence of filtering for each following cycle 2, 3 and so on. In one embodiment, during this process of repeatedly blocking and passing of the optical signal 115 over time, the monitor circuit 137 samples signal 305 to produce sample data 138 as in FIG. 4. An intensity reading for a given filter 122 can be a measure between a peak and subsequent valley or between a valley and subsequent peak of signal 305.

For example, as previously discussed and as shown in FIG. 3, signal 305 increases between time T1 and time T2. The monitor circuit 137 can be configured to measure the optical energy in a frame such as when filter 122-1 passes in a path of optical signal 115 by repeated sampling of signal 305 to identify the lowest value of the signal 305, which occurs around time T1. The identified low value represents a valley and relative "zero" of the detector 136 for filter 122-1. The monitor circuit 137 also monitors signal 305 in the frame to identify a subsequent highest value of the signal 305, which occurs at around time T2. The high value represents a peak for filter 122-1. A difference in the signal 305 values between this peak and the valley pair represents a measure of how much optical energy is detected by the detector 136 for the given filter. Or, alternately, the rate of change recorded in detector output can be monitored as an indicator of how much optical energy is being absorbed.

Signal 305 increases between time T3 and time T4. The monitor circuit 137 can be configured to measure the optical energy in a frame such as when filter 122-2 passes in a path of optical signal 115 by repeated sampling of signal 305 to identify the lowest value of the signal 305, which occurs around time T3. The identified low value represents a valley and relative "zero" of the detector 136 for filter 122-2. The monitor circuit 137 also monitors signal 305 to identify a subsequent highest value of the signal 305, which occurs at around time T2. The high value represents a peak for filter 122-2. A difference in the signal 305 between this peak and the valley pair represents a measure of how much optical energy is detected by the detector 136 for filter 122-2.

This monitor circuit 137 can be configured to repeat sampling of signal 305 for each of the different filters 122 on a continuous basis so that the analyzer system 100 continuously monitors the presence of different gases in sample 126 as it passes from inlet 127 through chamber 129 to outlet 128. Note again that measuring the optical energy between peak-valley pairs or valley-peak pairs to determine an absorbance of optical energy is shown by way of a non-limiting example only and that the signal 305 can be processed in a number of different ways to detect how much of the optical signal 115 passes through the sample 126 and/or how much is absorbed by the sample 126.

FIG. 4 is an example diagram illustrating sample data 138 according to embodiments herein. As shown, sample data 138-1 includes intensity readings associated with signal 305 for each of the filters 122 for cycle #1, sample data 138-2 includes intensity readings associated with signal 305 for each of the filters 122 for cycle #2, and so on. Sample data such as data 11, data 12, etc. for each successive filter 122 represents data collected by monitor circuit 137.

In one embodiment, data sample 138-1 can include sample information collected during cycle #1. For example, data 11 can include a pair of peak-valley readings for reference filter 122-1 in cycle #1, data 12 can include a pair of peak-valley readings for reference filter 122-2 in cycle #1, data 13 can include a pair of peak-valley readings for reference filter 122-3 in cycle #1, and so on.

In furtherance of such an embodiment, data sample 138-2 can include sample information collected during cycle #2. For example, data 21 can include a pair of peak-valley readings for reference filter 122-1 in cycle #2, data 22 can include a pair of peak-valley readings for reference filter 122-2 in cycle #2, data 23 can include a pair of peak-valley readings for reference filter 122-3 in cycle #2, and so on.

In this way, the monitor circuit 137 can store sample data for each of the cycles.

To reduce the amount of data stored in repository 180, the monitor circuit 137 can store sample data 138 in any of multiple different ways. For example, in one embodiment, the monitor circuit 137 collects the peak and valley values for each of the different filters 122 for cycle #1 and stores the sample data in repository 180. In following cycle #2, the monitor circuit 137 collects peak and valley values for each of the different filters 122 for cycle #2 and adds the collected peak and valley values for cycle #2 to those for cycle #1. The monitor circuit 137 repeats this process of collecting and summing the sample data such that, after K cycles, the sample data 138 in repository 180 includes a summation of K peak samples and a summation of K valley samples for filter 122-1, a summation of K peak samples and a summation of K valley samples for filter 122-2, a summation of K peak samples and a summation of K valley samples for filter 122-3, a summation of K peak samples and a summation of K valley samples for filter 122-4, and so on.

As previously discussed, after collection of the sample data 138, the analyzer 140 (FIG. 1) uses the collected sample data 138 to identify which type of matter such as gases are present in sample 126 and/or a concentration of the gases.

Figure 5:
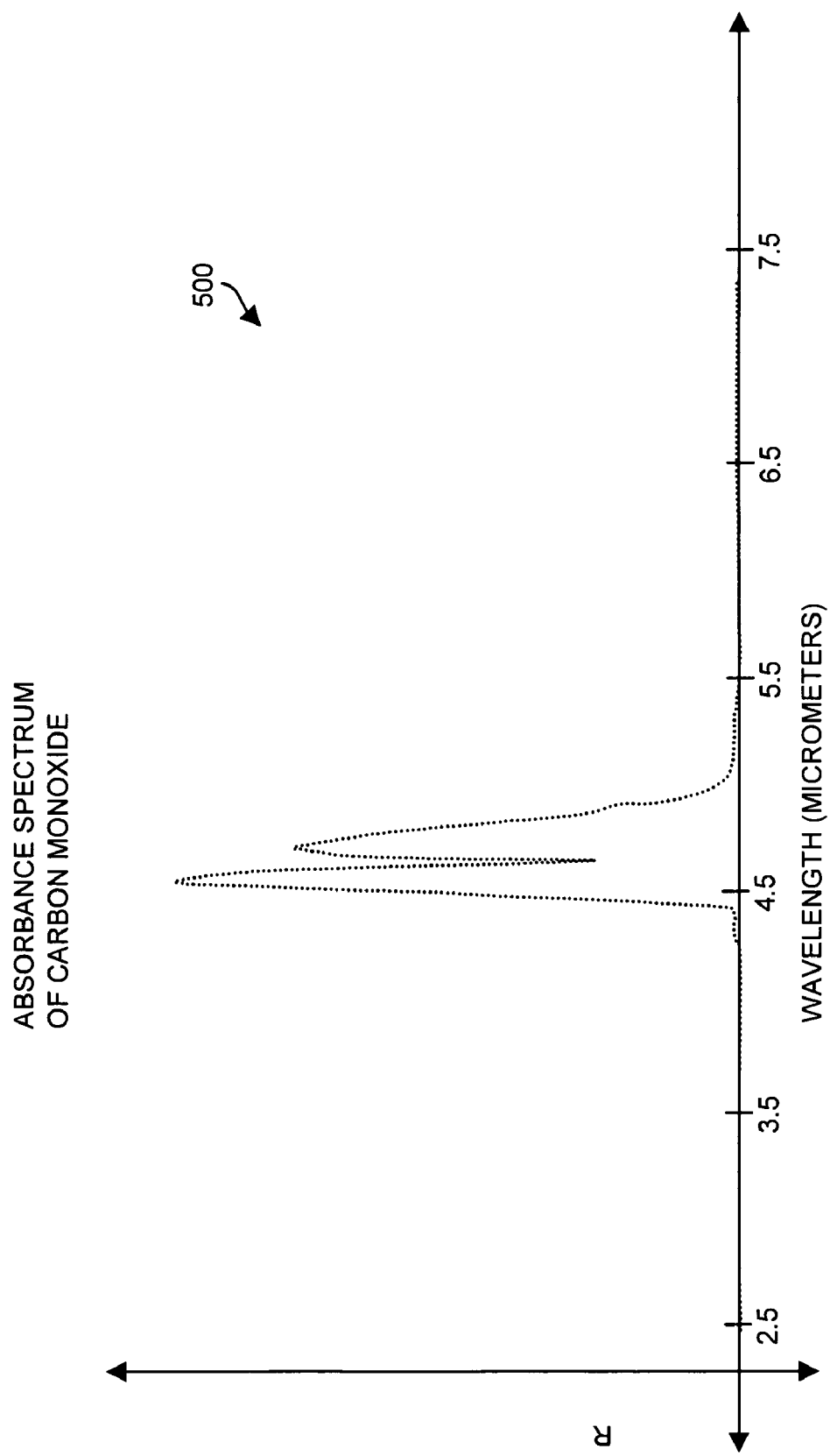
FIG. 5 is an example graph illustrating absorption of energy associated with carbon monoxide over a range of wavelengths.

FIG. 5 is an example graph 500 illustrating absorption of energy associated with carbon monoxide over a range of wavelengths. As shown, carbon monoxide absorbs optical energy in the range of optical wavelengths approximately between 4.4 and 4.8 micrometers.

Figure 6:
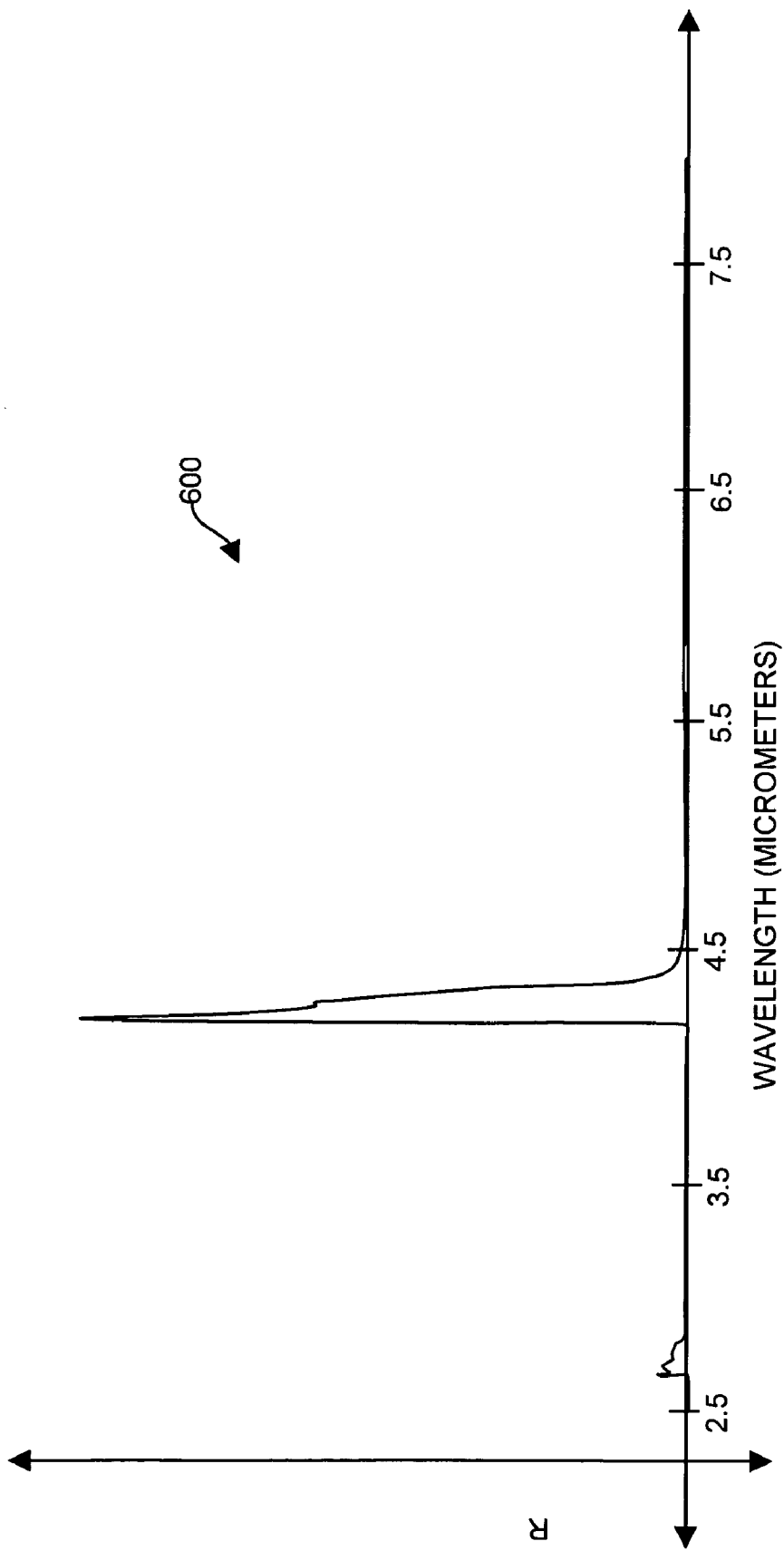
FIG. 6 is an example graph illustrating absorption of energy associated with carbon dioxide over a range of wavelengths.

FIG. 6 is an example graph 600 illustrating absorption of energy associated with carbon dioxide over a range of wavelengths. As shown, carbon dioxide absorbs optical energy in the range of optical wavelengths approximately between 4.2 and 4.5 micrometers.

Figure 7:
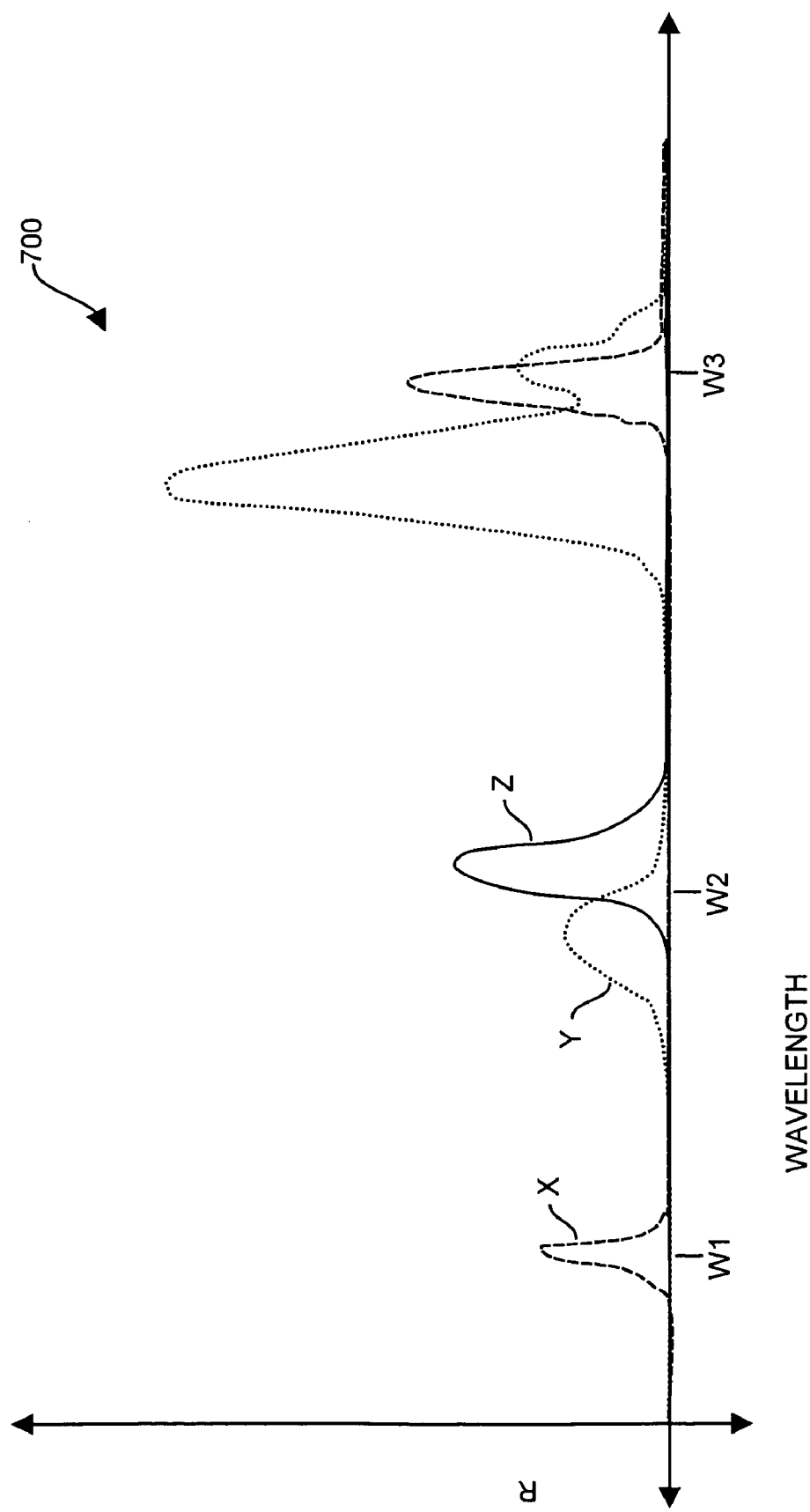
FIG. 7 is an example graph illustrating hypothetical energy absorption at different wavelengths for multiple different gas samples.

FIG. 7 is an example graph 700 illustrating energy absorption at different wavelengths for multiple different gases such as gas X, gas Y, and gas Z, potentially present in sample 126 passing through chamber 129. Note that this is only an example illustration of different gases and how they can absorb optical energy in the same wavelengths and thus "interfere" with each other.

As illustrated, certain gases can absorb optical energy at around the same wavelengths. For example, gas Y and gas Z both absorb optical energy in a range of wavelength values around wavelength W2. Also, gas Y and gas Z both absorb optical energy in a range of wavelength values around wavelength W3.

The following discussion presents an example of how to convert detected optical intensity values such as those in sample data 138 to one or more corresponding concentration measurements of gases present in sample 126. The first step is to determine the amount of energy that was absorbed by the gas sample. This is called the Absorbance, and it is defined as the log of the ratio of the intensity measured when there is no sample present (the Zero Intensity) divided by the intensity measured when the sample is present (Sample Intensity).

$$A = \log(I_o/I_s), \quad \text{(Equation 1)}$$

where A is the absorbance, $I_o$ is the intensity measured while sampling high purity zero air, and $I_s$ the intensity measured while sampling the gas of interest.

As long as one holds other parameters constant, the absorbance is a direct measure of concentration. Also, absorbance values are additive, so if two different gases both cause some attenuation or absorbance of the modulated optical signal 125 for a given filter 122, the total absorbance at that wavelength is the sum of the individual absorbance for each of the gases. This is referred to as interference. Analyzer 140 corrects for cross interferences between channels as discussed below.

To more accurately measure absorbance of the modulated optical signal 125, the analyzer 140 can be calibrated in accordance with a calibration procedure that establishes the relationship between the measured absorbance and the concentration of the target compound in the sample 126.

In one embodiment, the calibration procedure includes filling the chamber 129 with clean, so-called "zero" air that does not contain the target compound (Absorbance=0). The analyzer 140 records the detected signal for such a gas. In one embodiment, calibration includes calibrating the analyzer 140 at each of multiple different concentrations for each gas of interest that may be present in sample 126.

According to Beer's Law:

$$A = \epsilon bC, \quad \text{(equation 2)}$$

where A is absorbance, $\epsilon$ is the absorptivity of the gas of interest, b is the sample pathlength as a result of reflections between reflectors 131, and C is the concentration of the gas of interest.

Absorbance readings increase proportionally with increased concentrations of the target compound. In practice, some deviation from linearity may be observed.

As mentioned above, the analyzer 140 can be calibrated using multipoint calibration, using high purity zero air and a series of different concentrations of span gases in a factory setting.

In the field, it may be difficult for an average user to perform this type of calibration. Thus, field calibration procedures may be different than factory calibration procedures.

A so-called field zero procedure or calibration performed in the field can be similar to the factory zero as discussed above, except there is no assumption that the so-called "zero" air will be free of water. Also, instead of calibrating the analyzer 140 via testing of multiple concentrations for each target gas, the calibration procedure can include measuring a single target sample at a known concentration as the non-linearity detected during the factory calibration is repeatable.

As previously discussed, the reference wavelength for filter 122-1 and filter 122-2 is selected at a point in the optical spectrum where none of the possible target gases in the sample 126 is expected to cause absorbance. Changes in the intensity of the modulated optical signal 125 measured at the reference wavelength are assumed to occur because of fluctuations in behavior of the hardware such as the optical signal 115 source and detector 137 and are assumed to occur to the same degree in both the reference channels and sample channels. Reference channels refer to sampling of the modulated optical signal 125 via use of filter 122-1 and filter 122-2. Sample channels refer to sampling of the modulated optical signal 125 via use of filter 122-3, filter 122-4, etc. By recording the ratio of sample signal to reference signal (S/R), the impact of instrument drift or random interferences can be reduced.

Figure 8:
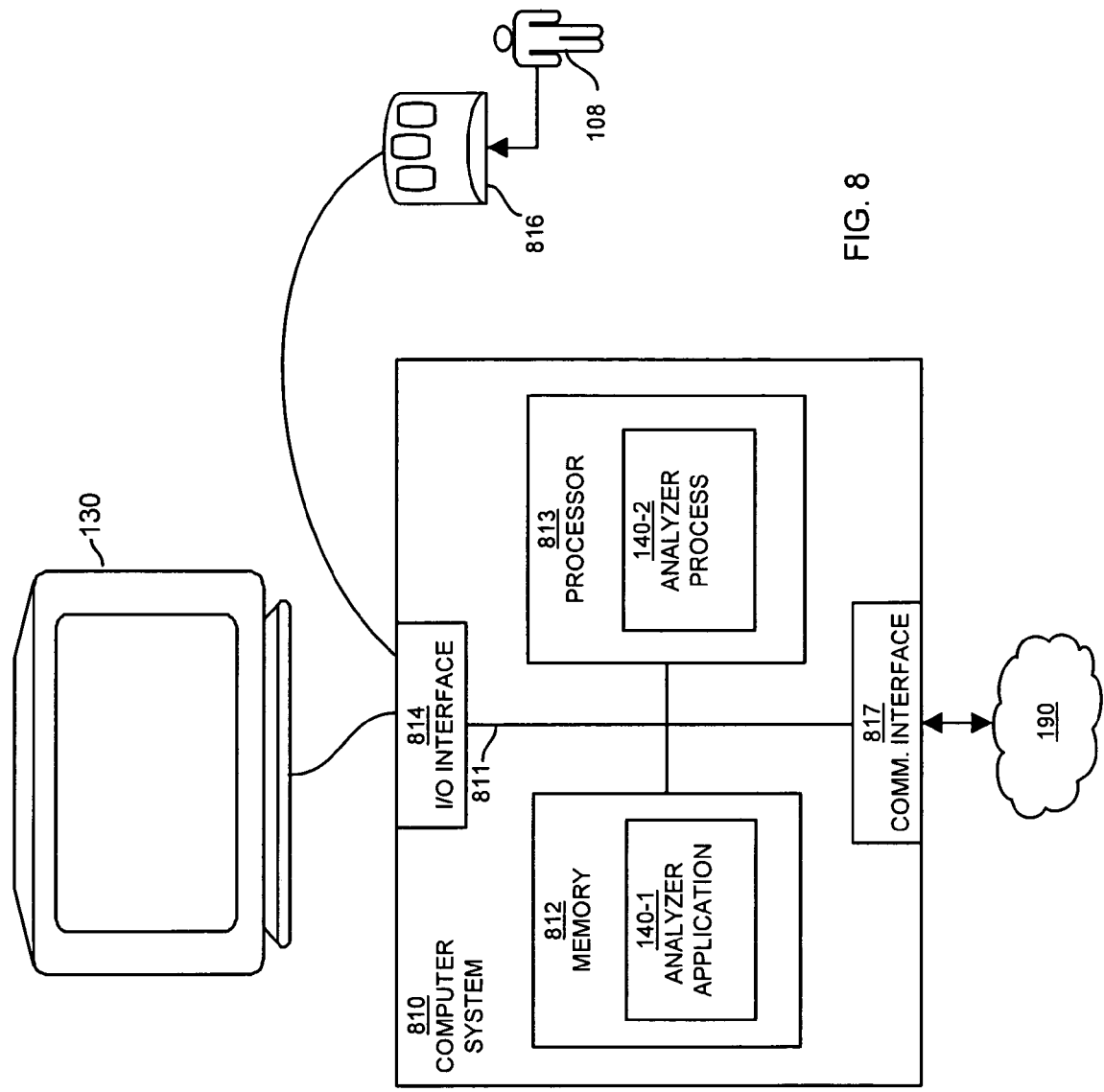
FIG. 8 is an example block diagram of a computer system configured with a processor and related storage to execute different methods according to embodiments herein.

FIG. 8 is a block diagram of an example architecture of a respective computer system 810 such as one or more computers, processes, etc., for implementing analyzer 140 according to embodiments herein. Computer system 810 can include one or more computerized devices such as personal computers, workstations, portable computing devices, consoles, network terminals, networks, processing devices, etc.

Note that the following discussion provides a basic example embodiment indicating how to carry out all or portions of the functionality associated with the analyzer 140 as discussed above and below. However, it should be noted again that the actual configuration for carrying out the analyzer 140 can vary depending on a respective application. For example, as previously discussed, computer system 810 can include one or multiple computers that carry out the processing as described herein.

As shown, computer system 810 of the present example includes an interconnect 811 coupling, memory system 812, a processor 813, I/O interface 814, and a communications interface. Computer system 810 can be an embedded in analyzer 140 or reside external to analyzer 140.

I/O interface 814 provides connectivity to peripheral devices such as repository 180 and other devices 816 (if such devices are present) such as a keyboard, mouse (e.g., selection tool to move a cursor), display screen 130, etc.

Communications interface 817 enables the analyzer application 140-1 of computer system 810 to communicate over network 190 and, if necessary, retrieve data, update information, etc., from different sources.

As shown, memory system 812 can be encoded with instructions associated with analyzer application 140-1. The instructions support functionality as discussed above and as discussed further below. The analyzer application 140-1 (and/or other resources as described herein) can be embodied as software code such as data and/or logic instructions on a tangible and/or intangible computer readable medium, media, etc. such as memory or on another computer readable medium that supports processing functionality according to different embodiments described herein.

During operation of one embodiment, processor 813 accesses memory system 812 via the use of interconnect 811 in order to launch, run, execute, interpret or otherwise perform the logic instructions of the analyzer application 140-1. Execution of the analyzer application 140-1 produces processing functionality in analyzer process 140-2. In other words, the analyzer process 140-2 represents one or more portions of the analyzer 140 performing within or upon the processor 813 in the computer system 810.

It should be noted that, in addition to the analyzer process 140-2 that carries out method operations as discussed herein, other embodiments herein include the analyzer application 140-1 itself such as the un-executed or non-performing logic instructions and/or data, etc. The analyzer application 140-1 may be stored on a computer readable medium such as a floppy disk, hard disk or in an optical medium. According to other embodiments, the analyzer application 140-1 can also be stored in a memory type system such as in firmware, read only memory (ROM), or, as in this example, as executable code within the memory system 812 (e.g., within Random Access Memory or RAM).

Functionality supported by analyzer 140 and, more particularly, functionality associated with analyzer 140 will now be discussed via flowcharts in FIGS. 9 through 10.

Figure 9:
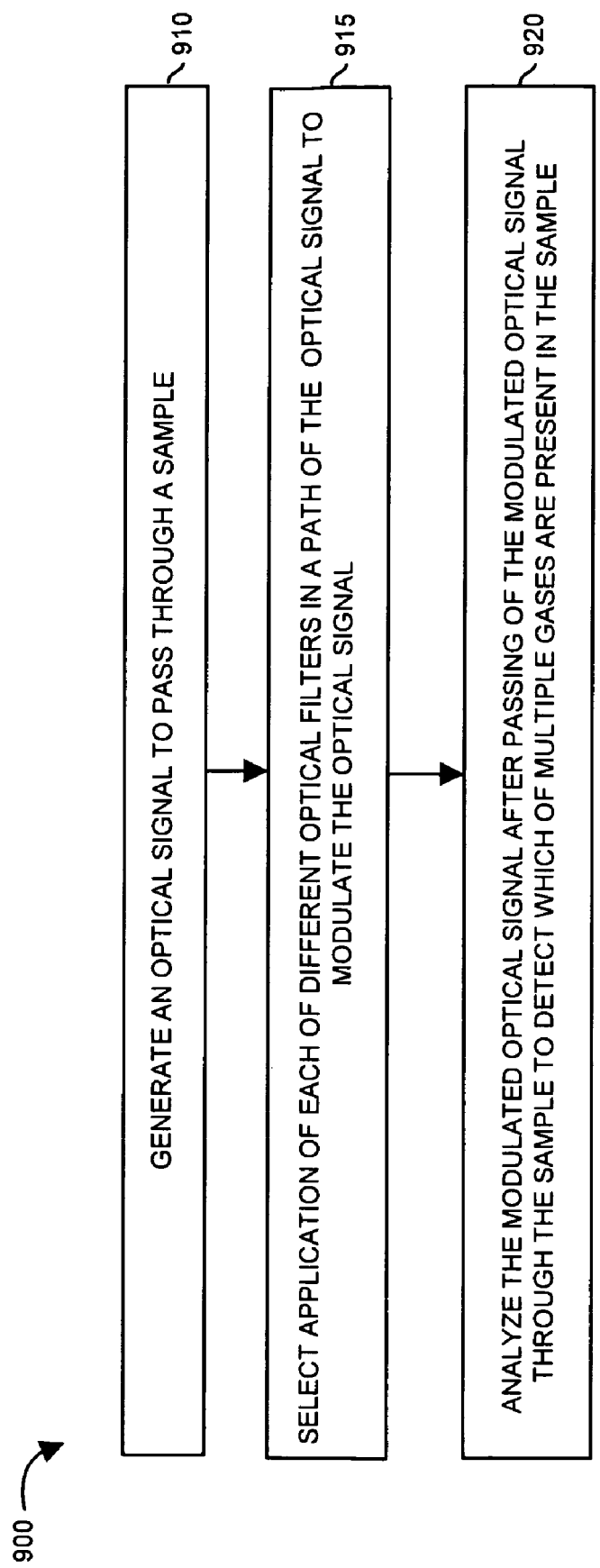
FIGS. 9 and 10 are example flowcharts illustrating methods according to embodiments herein.

More particularly, FIG. 9 is an example flowchart 900 illustrating operations associated with analyzer 140 according to embodiments herein. Note that flowchart 900 of FIG. 9 and corresponding text below may overlap with and refer to some of the matter previously discussed with respect to FIGS. 1-8. Also, note that the steps in the below flowcharts need not always be executed in the order shown.

In step 910, the analyzer 140 generates an optical signal 115 to pass through a sample 126.

In step 915, the analyzer 140 selects application of each of different optical filters 122 in a path of the optical signal 125 to produce modulated optical signal 125.

In step 920, the analyzer 140 analyzes the modulated optical signal 125 after passing of the modulated optical signal 125 through the sample 126 to detect which of multiple possible target gases are present in the sample 126.

Figure 10:
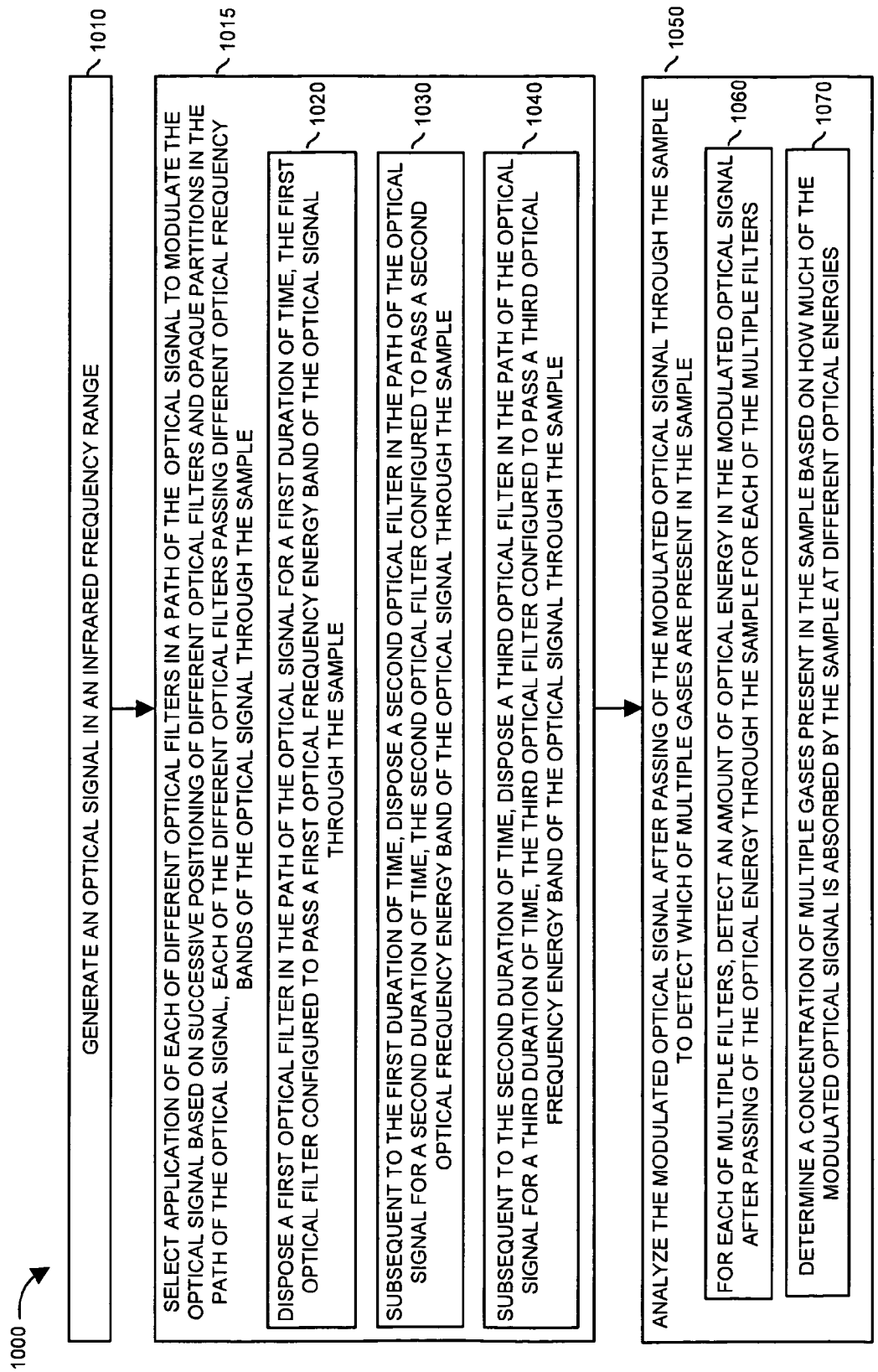

FIG. 10 is an example flowchart 1000 illustrating operations associated with analyzer 140 according to embodiments herein. Note that flowchart 1000 of FIG. 10 and corresponding text below may overlap with and refer to some of the matter previously discussed with respect to FIGS. 1-9. Also, note that the steps in the below flowcharts need not always be executed in the order shown.

In step 1010, the analyzer 140 generates an optical signal 115 in an infrared frequency range.

In step 1015, the analyzer 140 selects application of each of different optical filters 122 in a path of the optical signal 115 to produce modulated optical signal 125. Selecting the different filters 122 can include successive positioning of different optical filters 122 and opaque partitions 220 in the path of the optical signal 115. As previously discussed, each of the different optical filters 122 can be configured to pass a different optical frequency band of the optical signal 115 through the sample 126.

For example, in sub-step 1020, the analyzer 140 disposes a first optical filter such as filter 122-2 in the path of the optical signal 115 for a duration of time. The optical filter 122-2 is configured to pass a first optical frequency energy band of the optical signal 115 through the sample 126.

In sub-step 1030, subsequent to the first duration of time, the analyzer 140 disposes a second optical filter such as filter 122-3 in the path of the optical signal for a duration of time. The second optical filter can be configured to pass a second optical frequency energy band of the optical signal through the sample 126.

In step 1040, subsequent to the second duration of time, the analyzer 100 can dispose a third optical filter such as filter 122-4 in the path of the optical signal 115 for a duration of time. The third optical filter can be configured to pass a third optical frequency energy band of the optical signal through the sample 126.

Based on repeatedly passing the filter 122 in a path of the optical signal 115, the analyzer 140 produce modulated optical signal 125.

In step 1050, the analyzer 140 analyzes the modulated optical signal 125 after passing of the modulated optical signal 125 through the sample 126 to detect which of multiple gases are present in the sample 126.

In step 1060, for each of multiple filters, the analyzer 100 detects an amount of optical energy in the modulated optical signal 125 after passing of the optical energy through the sample 126 for each of the multiple filters 122.

In step 1070, the analyzer 140 determines a concentration of one or more gases present in the sample based on how much of the modulated optical signal 125 is absorbed by the sample 126 at different optical energies.

As discussed above in FIG. 1, optical components such as filters 122 and electrical circuits such as detector assembly 135, sample data processor 142, etc., in analyzer 140 enable detection and measurement of the specific example target gases noted above without use of a second analytical technology, such as gas filter correlation or UV spectroscopy. Specially chosen values of filters 122 and corresponding algorithms implemented by sample data processor 142 enable creation of a relatively simple and low-cost analyzer 140, which is able to detect concentrations of multiple different gas types in sample 126.

In one embodiment, note that the analyzer 140 can provide for internal compensation that allows low concentrations of targeted compounds to be detected and measured in the presence of high concentrations of other IR (Infrared) absorbing compounds, including gases such as water and carbon dioxide. For example, in accordance with embodiments as described herein, the analyzer 140 can be configured to provide the ability to measure a concentration of water directly such as by using a dedicated filter 122-3 without a need for implementing an external water measurement system in cases where the sample cell is operated at reduced pressure.

In yet further embodiments, note that analyzer 140 can include a water sensor to detect a level of water in the sample 126 prior to or after reaching chamber 129. When the water sensor detects the presence of water above a threshold value, the analyzer 140 can be configured to automatically shut down flow of the sample 126 through the chamber 129 to prevent damage, equipment failure, etc. caused by the presence of excess water.

Also, in accordance with embodiments herein, note that the analyzer 140 has the ability to measure certain target gases or components based on IR absorbance of component isotopes that are present at a low, but stable fraction of the total concentration of a corresponding compound.

Example Configuration

Referring again to FIG. 1, note that the analyzer 140 can include one or more unique features that extend the capability of analyzer 140 beyond those of conventional applications.

For example, as discussed above, the analyzer 140 can include a single optical filter assembly 120 including a series of multiple carefully selected optical filters 122. The filters 122 can be separated by a series of metal spokes such as opaque material to block light energy from passing so that the optical filter assembly 122 functions as both a "chopper" that modulates the IR signal and as a mechanism for rapidly changing which frequency band of optical signal 115 energy is passed through the sample 126.

Note that use of the optical filter assembly 120 is shown by way of non-limiting example only. In lieu of using the optical filter assembly 120, a conventional chopper wheel and filter wheel can be used to generate modulated signal 125 for passing through the sample 126. Other ways of producing and detecting different frequency bands also can be used.

In one embodiment, the optical filter assembly 120 can include one or more reference filters such as filter 122-1 and filter 122-2 for the S/R (Signal/Reference) corrections mentioned above. Measurements in those channels are used to correct for interference as previously discussed and as discussed below.

The analyzer 140 uses the analytic filters such as filters 122-3 through 122-12 to measure the target compounds and/or interfering gases that are potentially present in the sample 126. Implementing the optical filter assembly 120 to include reference filters 122-1 and 122-2 and analytic filters 122-3 through 122-12 according to embodiments herein enables detection of different gases using a single optical beam as generated by optical source 110. That is, the filters 122 on the optical filter assembly 120 of FIG. 1 move in and out of the optical path to create the different frequency band channels. Thus, the optical signal 115 and filters 112 serve as a way to create time-sliced reference channels and analytic channels depending on which of the respective filters 122 happens to be in the path of optical signal 115 at a particular time.

As mentioned, in accordance with the embodiment (as discussed above) in FIG. 1, the filter controller 155 of analyzer 140 initiates rotation of the optical filter assembly 120 to align filters 122 of the optical filter assembly 120 in the path of the optical signal 115 to filter the optical signal 115 at the different frequency bands. Rotation of the optical filter assembly 120 includes aligning a first filter 122-3 of the optical filter assembly 120 in the path of the optical signal 115 to measure absorbance by the sample 126 at the first frequency band followed by aligning a second filter 122-4 of the optical filter assembly 120 in the path of the optical signal 115 to measure absorbance by the sample 126 at the second frequency band followed by aligning a third filter 122-5 of the optical filter assembly 120 in the path of the optical signal 115 to measure absorbance by the sample 126 at the third frequency band, and so on. Even quick moving gases or evanescent gases are more likely to be detected.

In one embodiment, the analyzer 140 continuously measures absorbance of the optical signal at the different frequency bands over time. For example, the analyzer 140 collects absorbance measurement information for each of the filter channels for a first cycle, a second cycle, and so on.

The sample data processor 142 of analyzer 140 calculates the concentrations of multiple different types of gases potentially present in the sample 126 based at least in part on optical measurements obtained in the different cycles.

As will be discussed in more detail below, calculating the concentrations can include successively approximating the concentrations of the multiple types of gases in sample 126 based on collection of absorbance data over the multiple absorbance measurement collection cycles. Initial concentration values as generated by analyzer 140, such as when the analyzer is first turned on, may be inaccurate. However, the concentration values generated by analyzer 140 become more accurate over time using the successive approximation technique as described herein because the analyzer 140 converges on more accurate concentration values.

Also, by way of a non-limiting example, note again that the chamber 129 can be configured as a so-called multipass cell including reflectors 131 such as a series of mirrors that force the beam of radiation to bounce back and forth and make multiple passes through the sample gas 126 before reaching the output 128. By making multiple passes through the chamber 129, the effective path length is increased which, in turn, increases the opportunity for the IR radiation to interact with the sample 126. This increased path length improves the sensitivity of the analyzer 140 and its ability to detect even minute amounts of different target gases present sample 126.

Further, note that values for the optical filters 122 can be selected based on consideration of the infrared absorbance spectra for each targeted gas and the IR absorbance characteristics of non-target gases that are likely to be present in the intended application. If it were possible to select absorbance peaks that were completely unique to each compound potentially in sample 126, then the data processing performed by sample data processor 142 would be relatively simple. However, as it turns out, there is significant overlap in absorbance characteristics of the different gases that are typically found in sample 126 such as combustion effluent. Accordingly, interpretation of the signals for more multiple gases requires more complex data processing.

For example, if CO were the only compound that would absorb energy at 4.6 microns, then a bandpass filter could be selected with a center wavelength of 4.6 microns and none of the other gases would produce a signal on that particular channel.

As it turns out, however, water vapor and some other compounds do absorb some optical energy at 4.6 microns, and can potentially interfere with CO measurements taken at that wavelength band. By knowing the relative absorbance that each gas will exhibit at each wavelength featured in the optical filter assembly 120, a series of simultaneous equations can be generated for detecting concentrations of different target gases even though there happens to be interference amongst the channels.

By way of a non-limiting example, the following discussion illustrates an example algorithm and sets of equations for identifying concentrations of different target gases in accordance with embodiments herein.

Data Acquisition and Processing:

As described earlier, data collection and processing starts with intensity measurements. As shown in FIG. 3, the signal 305 monitored by detector 136 may appear similar in shape to a sine wave. The amplitude of signal 305 and the rate of change between adjacent peaks and valleys both indicate the relative amount of energy in a respective frequency band or channel that does not get absorbed by the sample 126.

Each peak of signal 305 corresponds to a specific optical filter 122 with a corresponding "rise" occurring when a corresponding filter passes in front of the optical signal 115 and the drop occurring while the optical signal 115 is blocked by one of the spokes or opaque regions of the optical filter assembly 120.

In one embodiment, the analyzer is configured to collect multiple intensity measurements for each rotation of the wheel. In order to filter out noise, the analyzer 140 can be configured to accumulate intensity readings for each optical filter, or channel, over a period of one second and then treat the accumulated data from one or more rotations as a single data point. In one embodiment, the analyzer 140 measures and collects intensity data for 30 rotations of the optical filter assembly 120 and uses the collected information as a single collection data point to identify concentration values.

After collecting intensity values over each of the channels, the sample data processor 142 performs a ratio correction of the intensities taken on each of the channels against an intensity measurement of the reference channel. This results in a correction for any hardware instability in analyzer 140.

In other words, the intensity values collected for the reference filter channel should be a known value assuming that operating parameters of the analyzer 140 have not changed since calibration. For example, if operating parameters such as a line voltage used by the optical source 110 to generate the optical signal 115, temperature of the analyzer 140 changes, etc., then such changes will show up or affect measurements from each of the channels including the reference channel. It can be assumed that all channels experience a same degree of change and that such a "drift" can be corrected from the analytic channels such as filter 122-3, 122-4, 122-5, etc., using the reference channel data.

In one embodiment, to correct for drift using the reference channel information, the sample data processor 142 of analyzer 140 converts each intensity reading to an absorbance and then subtracts any absorbance change that occurs in the reference channel from those that occur in the analytic measurement channels (e.g., filter 122-3, 122-4, 122-5, . . . ).

After the intensities are converted to an Absorbance value and any Absorbance value change that could be attributed to hardware variations has been removed, the next step is to correct for interferences amongst the different gas types. For example, as mentioned, sample readings taken with filter 122-4 can be used to calculate an amount of CO in the sample 126. Both water and $N_2O$ are potentially interfering components that can absorb optical energy in the frequency band associated with filter 122-4.

Prior to using the intensity readings taken with filter 122-4 to determine a concentration of CO in the sample, the sample data processor 142 reduces or corrects the intensity reading taken with filter 122-4 by accounting for absorbance of the optical signal 115 by the interfering gases, which in this example are water and $N_2O$. One way to identify absorption by the interfering component(s) is to utilize readings obtained from other filter channels such as one or more different frequency bands to determine a degree to which the interfering components have affected the channel of interest.

In other words, assume that the channel of filter 122-4 is the gas type of interest. Readings taken from other filter channels such as filter 122-3 and filter 122-9 can be used to adjust the intensity reading for filter 122-4 so that the adjusted measurement value can be used to generate a concentration value for CO. Each of the different channels can be corrected to remove interference in a similar manner. This is discussed in more detail below.

Channel to Channel Interference Corrections:

As mentioned, each channel or filter value can be selected for obtaining a relatively strong absorbance response when exposed to a specific gas of interest. However, note that all of the channels may show some amount of cross interference and may exhibit a small response to gases other than the intended target.

The signal information collected from each individual channel includes absorption information for the gas type associated with the channel plus the additive effects of any interferences. During a calibration phase, an analyzer 140 according to one embodiment herein quantifies the interferences when individually exposed to the different gas types. For example, the analyzer 140 measures each channel's response to each gas and develops an "interference table" or matrix that expresses each channel's relative sensitivity to each gas.

The signal created on any specific channel by any given gas mixture is dependent on the concentration of each gas in the mixture, and on the sensitivity of that specific channel to each gas that is present. As an example, if channel #1 such as filter 122-5 is designed to measure $CO_2$, the output from channel #1 can be designated as A1total and would actually be composed of one large signal created by $CO_2$ plus a series of smaller signals created by other gases assuming that the other interfering gases are present in the sample 126.

In accordance with one embodiment, the sample data processor 142 takes the total signal generated by a given channel and subtracts out the portion created by each interfering gas, leaving just the signal or value representing absorption by the intended target gas for the specific channel.

By way of a non-limiting example, assume that the gas analyzer 140 includes 3 channel filters (and a reference filter to adjust for drift) designed to measure $CO_2$, $SO_2$ and $NO_2$.

In general, the analyzer 140 measures intensities of the different channels, converts the channel measurement values to absorbance, makes interference corrections using the reference channel, and then converts the corrected absorbance values to concentration readings for the different possible gases present in the sample 126.

In one embodiment, before making any measurements, the analyzer 140 is calibrated with known concentrations of the different possible gases of interest to determine the sensitivity of each channel to each of the individual gases that might be present in a sample. The analyzer 140 stored the calibration information into a table called an interference table. For a three-sensor system, the interference table might appear as follows:

|  | Sensor 1 (Targets $CO_2$) | Sensor 2 (Targets $SO_2$) | Sensor 3 (Targets $NO_2$) |
| --- | --- | --- | --- |
| Gas 1 ($CO_2$) | 1.0 | 0.3 | 0.4 |
| Gas 2 ($SO_2$) | 0.2 | 1.0 | 0.2 |
| Gas 3 ($NO_2$) | 0.3 | 0.1 | 1.0 |

Each sensor, or channel, has been referenced against its intended target, so that the CO2 sensor has a response of 1.0 to $CO_2$, the $SO_2$ sensor has a response of 1.0 to $SO_2$, and so on. In this case, sensor #1, which is designed to detect $CO_2$ also "sees" $SO_2$ and $NO_2$, but the response to $SO_2$ is only 20% of that seen with $CO_2$ and the response to $NO_2$ is 30% of that seen with $CO_2$. Sensor #2 is designed to respond to $SO_2$, but also has some response to both $NO_2$ and $CO_2$. Sensor #3 is designed to detect $NO_2$ but has significant response to $CO_2$ and also some response to $SO_2$.

Assume that the total signal generated by any one sensor is the sum of the responses generated by each individual gas present in the sample 126. Thus, in the context of the present example, the equations would be as follows:

$$A1total = A1CO_2 + A1SO_2 + A1NO_2$$

$$A2total = A2CO_2 + A2SO_2 + A2NO_2$$

$$A3total = A3CO_2 + A3SO_2 + A3NO_2$$

Where, for example, A1total is the signal read from sensor #1 and it is composed of the sum of absorbance by $CO_2$, $SO_2$, and $NO_2$.

To separate the signals, the sample data processor 142 sets up a series of simultaneous equations using the coefficients from the table.

Again, using the hypothetical example above, the sample data processor 142 sets up three equations and creates a loop that will "solve" the equations multiple times. Before entering the loop, the sample data processor 142 obtains the "total" sensor data (A1total, A2total, and A3total) and then, on each pass through the loop, the sample data processor 142 plugs in whatever concentration data is available at that time. For the first equation, the sample data processor 142 assumes that the total signal is generated by the target gas (disregarding interferences) and assumes that the other concentrations are zero. With each pass through the loop, the sample data processor 142 obtains new absorbance measurement data that will then be available for the next iteration. On the second pass, the sample data processor 142 now has estimated concentrations for each gas, so the sample data processor 142 can apply the relative response data from our interference matrix and calculate the amount of interference that each gas would create on each channel. This will only be a rough approximation, but with each successive pass through the loop, the approximation of concentrations of different types of gases in sample 126 gets better over time.

Intensity measurements taken at the ten analytical wavelengths (e.g., filter 122-3 through filter 122-12) are ratioed against the intensity measurement taken at the reference wavelength to correct for hardware instability and the measurements are then converted to absorbance values. Since absorbances are additive, the sample data processor 142 can then correct for interferences using a variation of successive approximations. Once the analyzer 140 has an interference corrected absorbance value for each target gas, the analyzer 140 then converts that value over to a concentration reading.

Calculating Concentrations:

Theoretically, the relationship between IR absorbance and gas concentration would be a straight-forward linear conversion. In that case, each channel could be calibrated using a zero gas that contains no IR absorbing compounds and single span gas containing a known concentration of the target. In the real world however, there is some nonlinearity in the response curve and multi-point calibration using a zero point and at least three span concentrations is required to achieve satisfactory levels of accuracy.

In certain cases, since high purity zero air may be difficult to obtain, it may be difficult to perform a multi-point calibration at a field site where the analyzer 140 is in use. However, a factory zero and a full multi-point calibration are performed on each unit before shipping of an analyzer 140 for use in the field.

In one embodiment, the "factory calibration" procedure requires first measuring a so-called zero-absorbance using an extremely high-grade zero air that contains essentially no IR absorbing contaminants. For the factory span procedure, calibration can include measuring the absorbance for all twelve channels at three concentrations of each target gas and at three concentrations of each expected interfering compound. Measurement of the actual absorbance for known gas concentrations enables creation of an interference table and coefficients as discussed above, and also allows us to develop a curve of absorbance versus concentration for each of the target compounds. In one embodiment, all of the factory data is loaded into a repository such as non-volatile memory of the analyzer 140. The user has the ability to "fine tune" the zero and the slope of the response curve using calibration gases that are more readily available.

The user, or field, zero procedure assumes that the "zero" air will contain some amount of water vapor (which causes interference). However, the gas should be free of any other IR absorbing compounds.

The step-by-step procedures for calculating the zero are included in Appendix A. Basically, the analyzer 140 takes intensity readings on all channels, converts the readings to absorbances, and then calculates the concentration of water in the zero air based on the absorbance for a given frequency band.

After determining the concentration of water, the analyzer 140 can account for the IR absorbance that is caused by water on each channel. Using that information, the analyzer 140 subtracts out the water interference from all channels to give us new "zero" absorbance values. The new calibration values such as "field zero" absorbance values can be saved as a separate table along with the zero absorbance values determined at the factory. In one embodiment, the operator of analyzer 140 has the option of going back and using factory calibration values if desired, rather than using the field calibration values.

The field span adjustments can occur in two different ways. If the operator introduces a single span gas, the absorbance is measured on all 12 channels and the interference correction table discussed above is corrected for changes that may have occurred since the table was first created at the factory. Once the interference table has been updated, the analyzer calculates the span gas concentration using the factory established curve of concentration versus absorbance. The calculated concentration is compared to the true span gas concentration, as entered by the operator. If the reading is inaccurate, a "span factor" which is the ratio of actual concentration divided by the calculated concentration is determined. This span factor will then be used to correct all readings for that particular gas. So for example, if a span gas containing 100 ppm (part per million) of CO produces a reading of 90 ppm using the factory calibration, a span factor of 1.111 (100/90=1.111) will be applied to all CO measurements.

If the operator introduces a span gas containing more than one target compound, it is not possible to adjust the interference table. So, the analyzer 140 can skip that step and simply calculates the span factors for each of the compounds present in the span mix. Details of the data processing, interference corrections, and calibration procedures are described in mathematical detail below.

Figure 11:
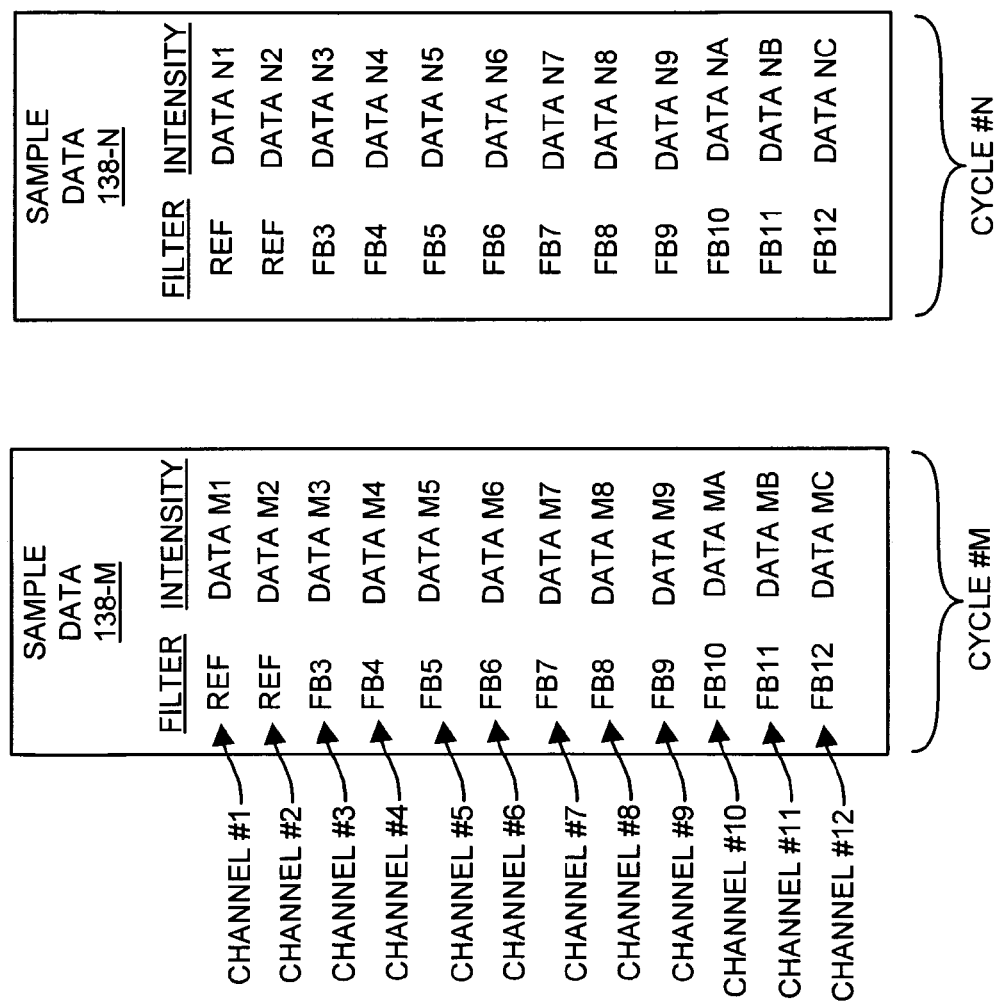
FIG. 11 is an example diagram illustrating sample data collected for multiple cycles according to embodiments herein.

FIG. 11 is an example diagram illustrating sample data collected over multiple cycles according to embodiments herein.

As previously discussed, the sample data 138-M can include one or more measurements of detected optical energy at the different frequency bands of optical filter assembly 120. For cycle #M, DATA M2 of data sample 138-M represents one or more optical intensity readings for the reference channel or channel #2, DATA M3 of data sample 138-M represents one or more optical intensity readings for channel #3, DATA M4 of data sample 138-M represents one or more optical intensity readings for channel #4, DATA M5 of data sample 138-M represents one or more optical intensity readings for channel #5, and so on.

Sample data 138-N represents sample data collected in cycle #N. Assume that cycle #N occurs after cycle #M. In one embodiment, cycle #N is the next cycle following cycle #M.

Note that the sample data 138-N also includes one or more measurements of detected optical energy at the different frequency bands of optical filter assembly 120. For cycle #N, DATA N2 represents one or more optical intensity readings for the reference channel or channel #2, DATA N3 represents one or more optical intensity readings for channel #3, DATA N4 represents one or more optical intensity readings for channel #4, DATA N5 represents one or more optical intensity readings for channel #5, and so on.

Figure 12A:
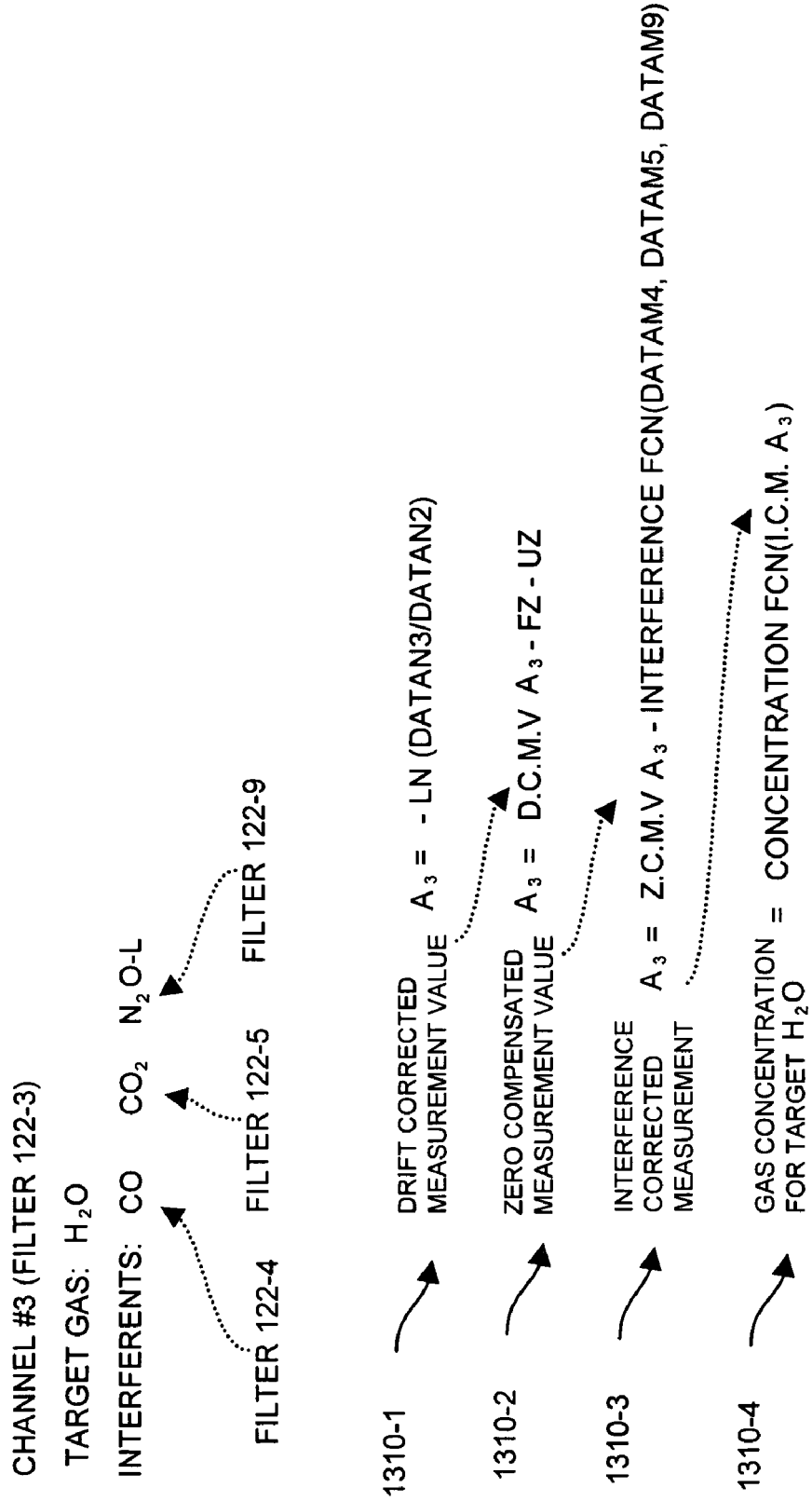
FIGS. 12A, 12B, and 12C are example diagrams illustrating generation of concentration values for different target gases based on data collected from multiple cycles according to embodiments herein.

FIG. 12A is an example diagram of equations 1310 illustrating use of sample data 138 as collected over multiple cycles to determine concentrations for a given one of multiple target gases according to embodiments herein. For example, the sample data processor 142 uses equations 1310 to determine a concentration of water present in sample 126. As indicated, the analyzer 140 uses filter 122-3 to collect measurements of how much of optical signal 115 passes though sample 126. Other gas types that also absorb optical energy in the frequency band of filter 122-3 include target gases CO, $CO_2$, and $N_2O$.

As indicated by equation 1310-1, the sample data processor 142 initially corrects the intensity measurement data obtained on channel #3. For example, the sample data processor 142 produces a drift corrected measurement value based on DATA N3 and DATA N2 (See FIG. 11) as collected during cycle #N.

As indicated by equation 1310-2, the sample data processor 142 utilizes the drift corrected measurement value obtained via equation 1310-1 to produce a zero compensated measurement value. In general, the "F" term such as FZ in equation 1310-2 is a factory calibration term obtained when the chamber 129 is dry and "zero" gas is present in the chamber 129. The "U" term such as UZ in equation 1310-2 is a user calibration term obtained when the chamber is wet and "zero" gas is present in the chamber 129. The zero compensated measurement value for channel #3 represents absorbance by water as well as CO, $CO_2$, and $N_2O$.

As indicated by equation 1310-3, the sample data processor 142 utilizes the zero compensated measurement value for channel #3 as well as an interference function to correct the respective channel for interference caused by other interfering gases. In other words, equation 1310-3 enables the analyzer 140 to produce a value representing how much optical energy is absorbed by the target gas assigned to the channel.

For example, the sample data processor 142 utilizes an interference function and data obtained in an earlier cycle M to subtract out any absorption caused by any interference gases such as CO, $CO_2$, and $N_2O$. The interference corrected measurement in equation 1310-3 represents absorption by the target gas, $H_2O$, associated with channel #3.

As indicated by equation 1310-4, the sample data processor 142 utilizes the interference corrected measurement value to generate a concentration value for the target gas. For example, if desired, the sample data processor 142 can use the interference corrected measurement in a concentration function to determine an amount of water in the sample 126 for cycle N.

Figure 12B:
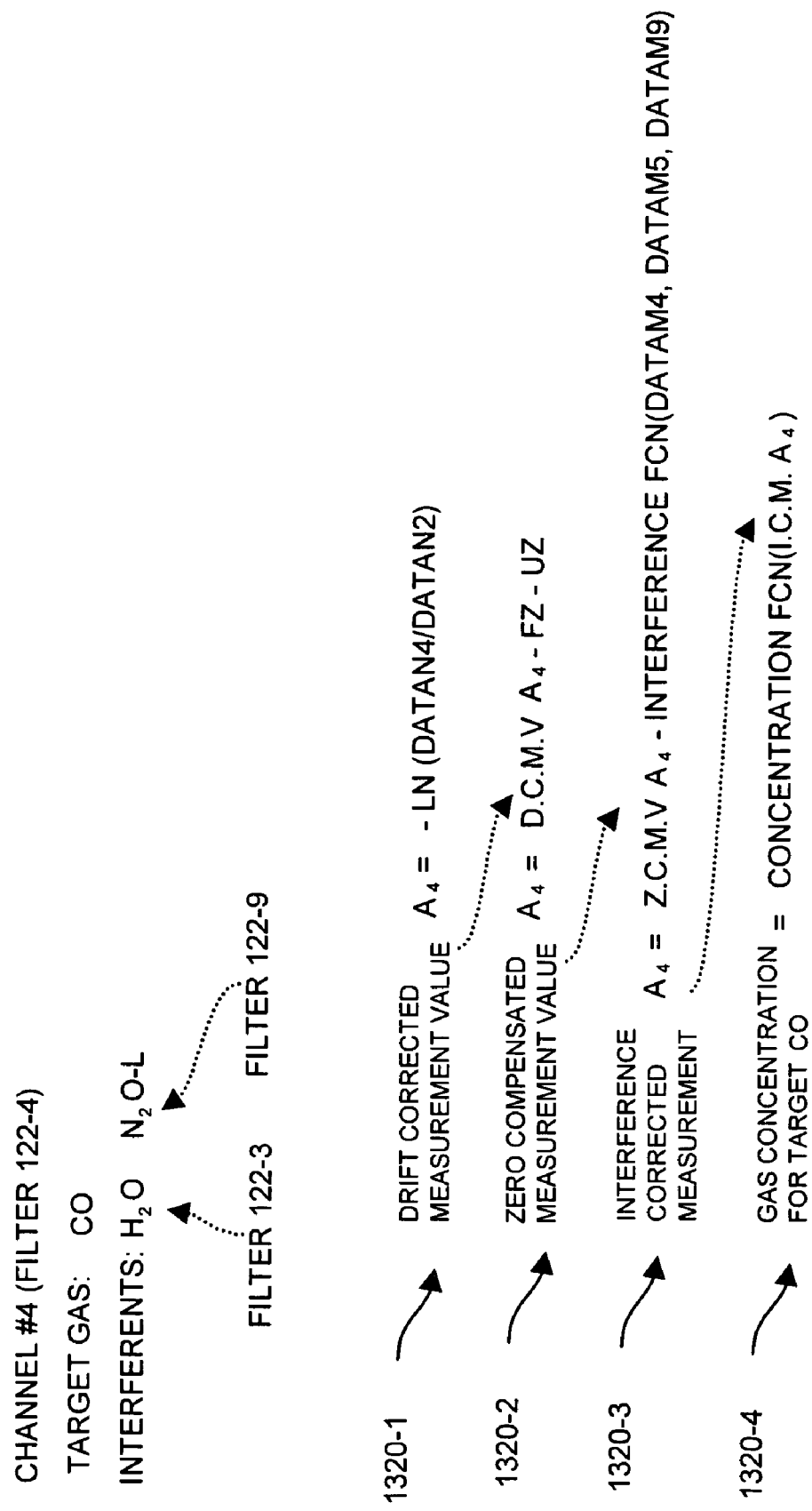

FIG. 12B is an example diagram including equations 1320 illustrating use of sample data 138 as collected over multiple cycles to determine a concentration of a target gas according to embodiments herein. In a similar manner as discussed above for water, the sample data processor 142 uses equations 1320 to determine a concentration of carbon monoxide present in sample 126.

As indicated, the analyzer 140 uses filter 122-4 to collect measurements of how much of optical signal 115 passes though sample 126. Other gas types that also absorb optical energy in the frequency band of filter 122-4 include target gases $H_2O$ and $N_2O$.

As indicated by equation 1320-1, the sample data processor 142 corrects the intensity measurement data obtained on channel #4. For example, the sample data processor 142 produces a drift corrected measurement value based on DATA N4 and DATA N2 (See FIG. 11) as collected during cycle #N.

As indicated by equation 1320-2, the sample data processor 142 utilizes the drift corrected measurement value obtained via equation 1320-1 to produce a zero compensated measurement value. In general, the "F" term in equation 1320-2 is a factory calibration term obtained when the chamber 129 is dry and "zero" gas is present in the chamber 129. The "U" term in equation 1320-2 is a user calibration term obtained when the chamber is wet and "zero" gas is present in the chamber 129. The zero compensated measurement value for channel #4 represents absorbance by CO as well as $H_2O$ and $N_2O$.

As indicated by equation 1320-3, the sample data processor 142 utilizes the zero compensated measurement value for channel #4 as well as an interference function to correct the respective channel for interference caused by other interfering gases. For example, the sample data processor 142 utilizes an interference function and data obtained in an earlier cycle M to subtract out any absorption caused by any interference gases such as $H_2O$ and $N_2O$. The interference corrected measurement in equation 1320-3 represents absorption by the target gas CO associated with channel #4.

As indicated by equation 1320-4, the sample data processor 142 utilizes the interference corrected measurement value to generate a concentration value for the target gas. For example, the sample data processor 142 uses the interference corrected measurement in a concentration function to determine an amount of carbon monoxide in the sample 126 for cycle N.

Figure 12C:
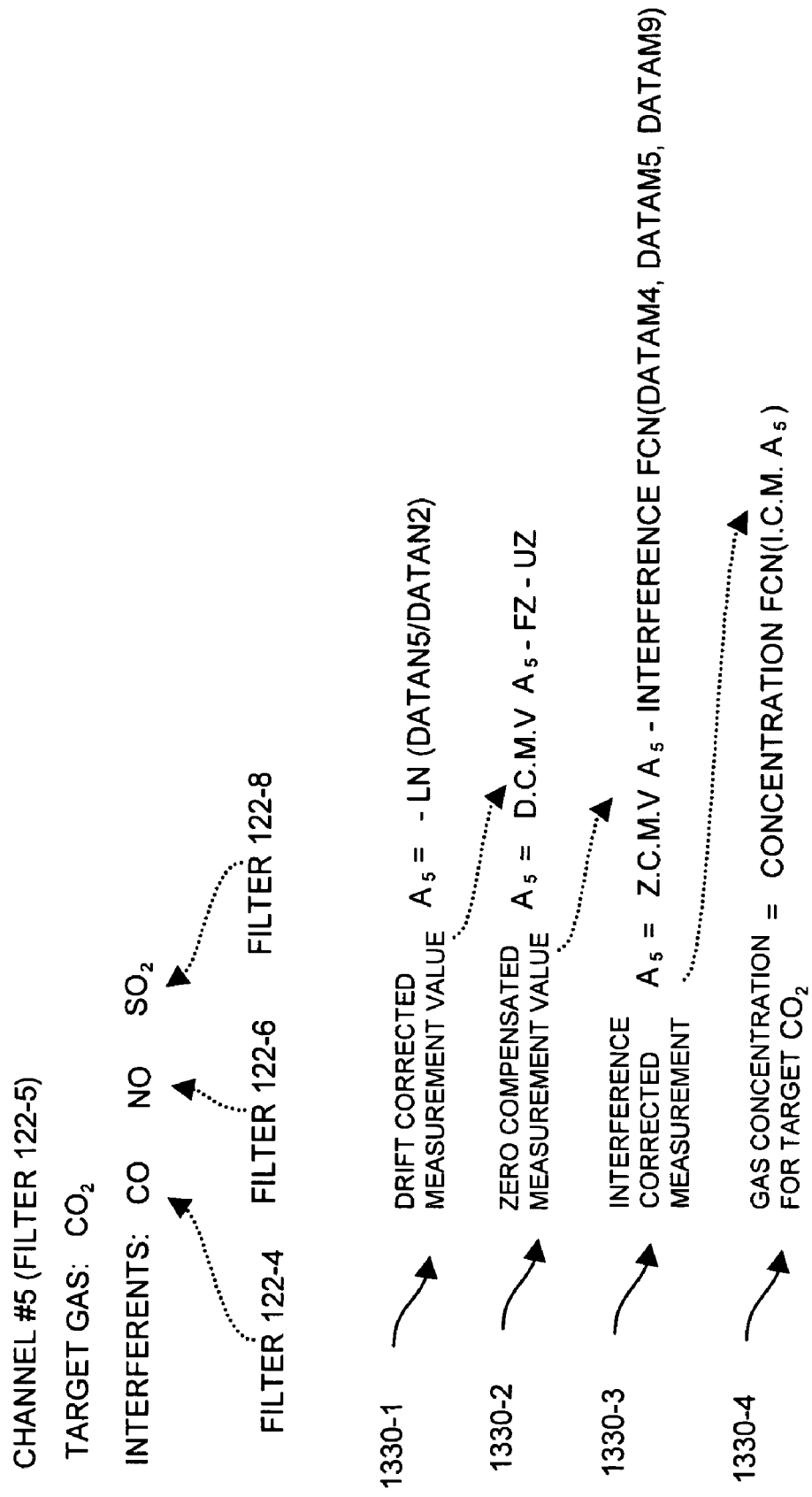

FIG. 12C is an example diagram including equations 1330 illustrating use of sample data 138 as collected over multiple cycles to determine a concentration of a target gas according to embodiments herein. In a similar manner as discussed above, the sample data processor 142 uses equations 1330 to determine a concentration of carbon dioxide present in sample 126.

As indicated, the analyzer 140 uses filter 122-5 to collect measurements of how much of optical signal 115 passes though sample 126. Other gas types that also absorb optical energy in the frequency band of filter 122-5 include target gases CO, NO, and $SO_2$.

As indicated by equation 1330-1, the sample data processor 142 corrects the intensity measurement data obtained in channel #5. For example, the sample data processor 142 produces a drift corrected measurement value based on DATA N5 and DATA N2 (See FIG. 11) as collected during cycle #N.

As indicated by equation 1330-2, the sample data processor 142 utilizes the drift corrected measurement value obtained via equation 1330-1 to produce a zero compensated measurement value. In general, the "F" term in equation 1330-2 is a factory calibration term obtained when the chamber 129 is dry and "zero" gas is present in the chamber 129. The "U" term in equation 1330-2 is a user term obtained when the chamber is wet and "zero" gas is present in the chamber 129. The zero compensated measurement value for channel #3 represents absorbance by $CO_2$ as well as CO, NO, and $SO_2$.

As indicated by equation 1330-3, the sample data processor 142 utilizes the zero compensated measurement value for channel #5 as well as an interference function to correct the respective channel for interference caused by other interfering gases. For example, the sample data processor 142 utilizes an interference function and data obtained in an earlier cycle M to subtract out any absorption caused by any interfering gases such as CO, NO, and $SO_2$. The interference corrected measurement in equation 1320-3 represents absorption by the target gas $CO_2$ associated with channel #5.

As indicated by equation 1330-4, the sample data processor 142 utilizes the interference corrected measurement value to generate a concentration value for the target gas. For example, the sample data processor 142 uses the interference corrected measurement in a concentration function to determine an amount of carbon dioxide in the sample 126 for cycle N.

In a similar manner, the analyzer 140 utilizes similar equations to perform calculations for each of the other channels to determine concentrations of other gases in sample 126.

Appendix A includes more specific details indicating how to convert collected sample data 138 on multiple channels into corresponding concentration measurements.

FIG. 13 includes a listing of example coefficients used by sample data processor 142 of analyzer 140 to determine the concentrations for each of the different target gases of interest. As mentioned above, the analyzer 140 creates the table of coefficients during calibration. Of course, values for the coefficients in table 1300 will vary depending on the actual filters 122 used to filter optical signal 115.

Figure 14:
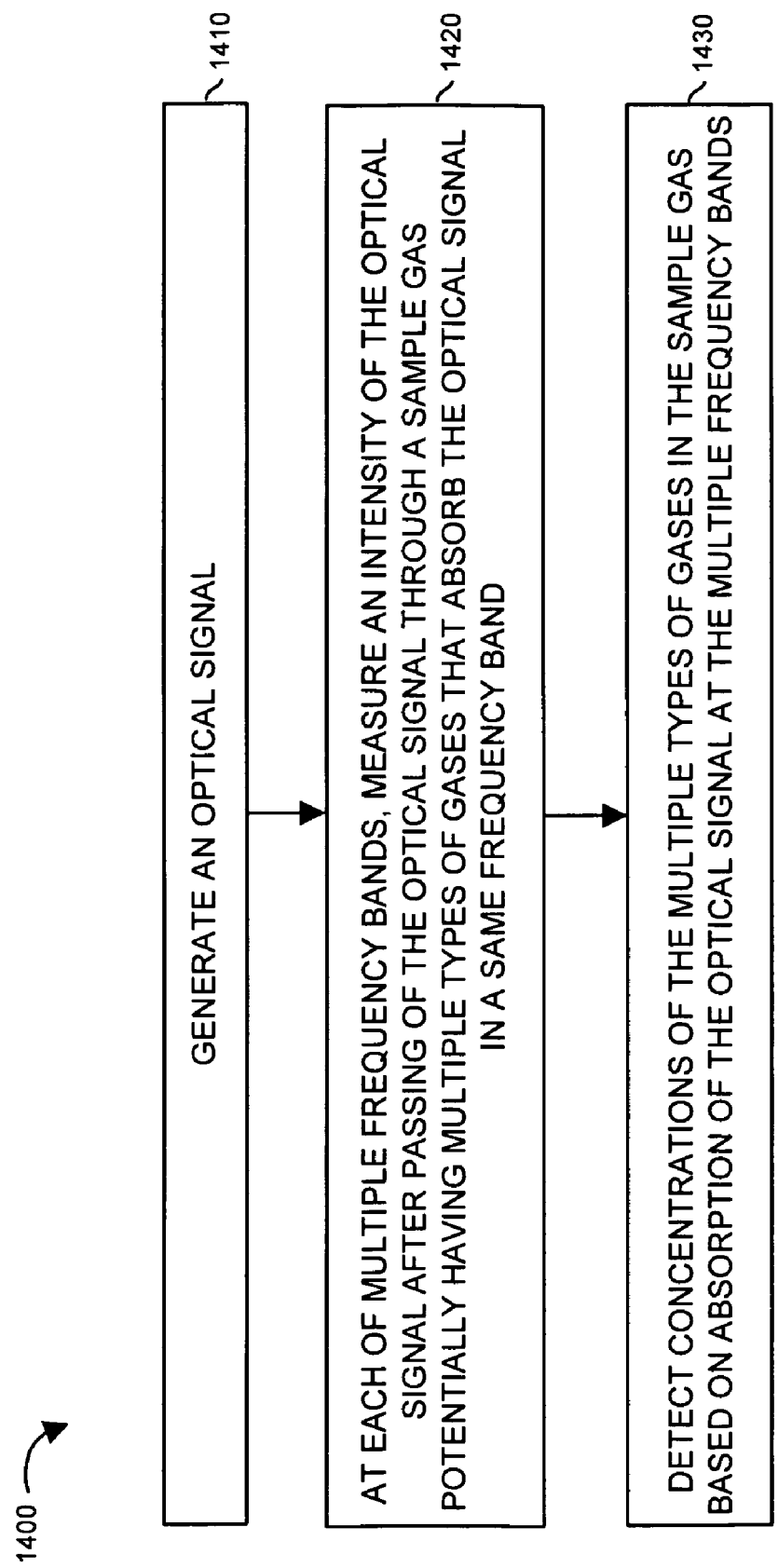
FIGS. 14-17 are example flowcharts illustrating methods for determining concentration(s) of one or more target gases in a sample according to embodiments herein.

FIG. 14 is an example flowchart 1400 illustrating operations associated with analyzer 140 according to embodiments herein. Note that flowchart 1400 of FIG. 14 and corresponding text below may overlap with and refer to some of the matter previously discussed with respect to the figures as discussed above. Also, note that the steps in the below flowcharts need not always be executed in the order shown.

In step 1410, the analyzer 140 generates an optical signal 115.

In step 1420, at each of multiple frequency bands, the analyzer 140 measures an intensity of the optical signal 115 after passage of the optical signal through a sample 126 potentially having multiple types of gases that absorb the optical signal in a single frequency band.

In step 1430, the analyzer 140 detects concentrations of the multiple types of gases in the sample 126 based on absorption of the optical signal 115 at the multiple frequency bands.

Figure 15:
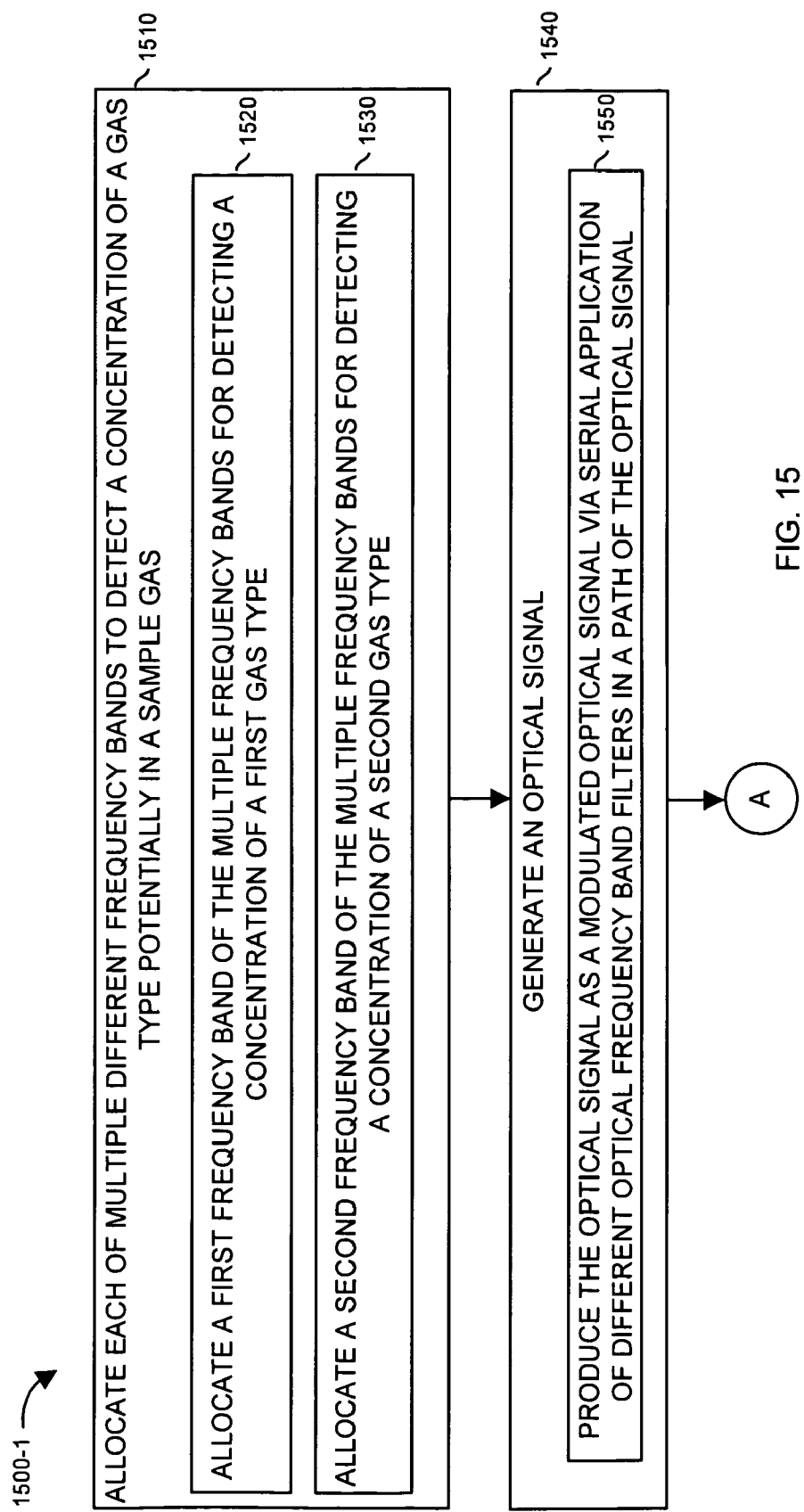
Figure 16:
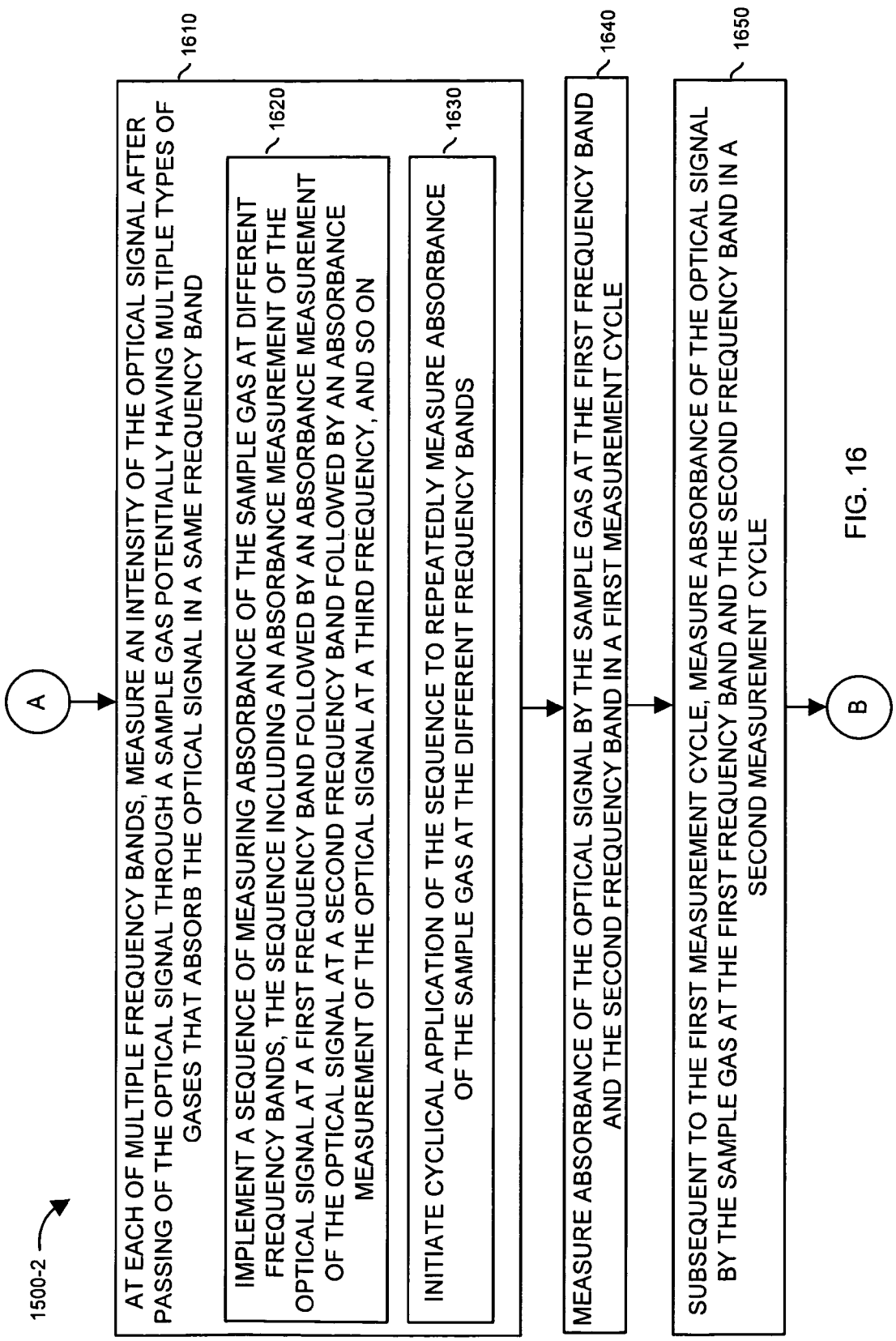
Figure 17:
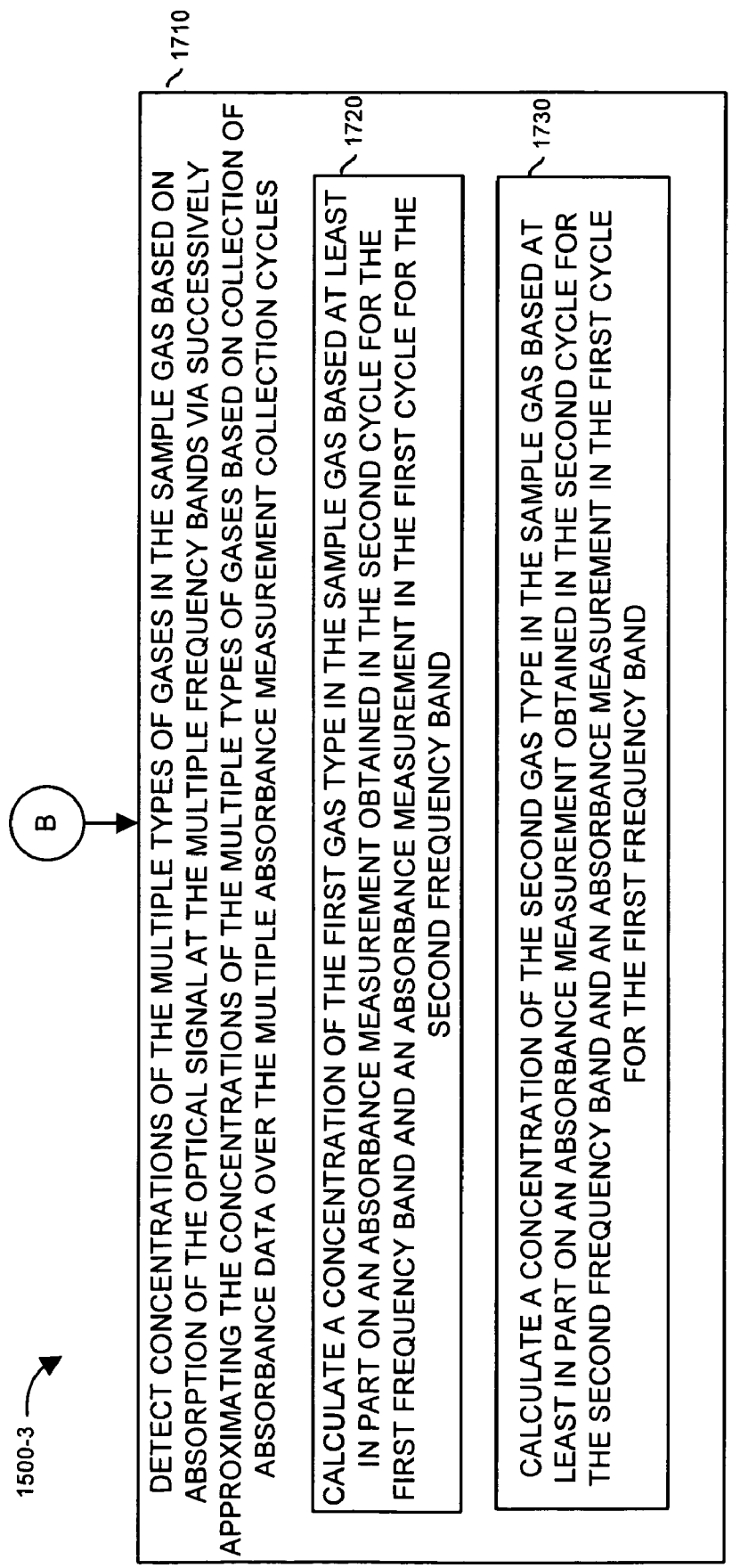

FIGS. 15, 16, and 17 combine to form a flowchart 1500 illustrating operations associated with analyzer 140 according to embodiments herein. Note that flowchart 1500 and corresponding text below may overlap with and refer to some of the matter previously discussed with respect to the figures as discussed above. Also, note that the steps in the below flowcharts need not always be executed in the order shown.

In step 1510, the analyzer 140 allocates or designates each of multiple different frequency bands to detect a corresponding concentration of a gas type potentially in sample 126.

In sub-step 1520, the analyzer 140 allocates a first frequency band of the multiple frequency bands for detecting a concentration of a first gas type.

In sub-step 1530, the analyzer 140 allocates a second frequency band of the multiple frequency bands for detecting a concentration of a second gas type.

In step 1540, the analyzer 140 generates an optical signal 115.

In sub-step 1550, the analyzer 140 produces the optical signal 115 as a modulated optical signal 115 via serial application of different optical frequency band filters in a path of the optical signal 115.

In step 1610, at each of multiple frequency bands, the analyzer 140 measures an intensity of the optical signal 115 after passage of the optical signal 115 through a sample 126 potentially having multiple types of gases that absorb the optical signal in a single frequency band.

In sub-step 1620, the analyzer 140 implements a sequence of measuring absorbance of the sample gas at different frequency bands. The sequence can include an absorbance measurement of the optical signal at a first frequency band followed by an absorbance measurement of the optical signal at a second frequency band followed by an absorbance measurement of the optical signal at a third frequency, and so on.

In sub-step 1630, the analyzer 140 initiates cyclical application of the sequence to repeatedly measure absorbance of the sample 126 at the different frequency bands.

In step 1640, the analyzer 140 measures absorbance of the optical signal 115 by the sample 126 at the first frequency band and the second frequency band in a first measurement cycle.

In step 1650, subsequent to the first measurement cycle, the analyzer 140 measures absorbance of the optical signal 115 by the sample 126 at the first frequency band and the second frequency band in a second measurement cycle.

In step 1710, the analyzer 140 detects concentrations of the multiple types of gases in the sample gas based on absorption of the optical signal at the multiple frequency bands via successively approximating the concentrations of the multiple types of gases based on collection of absorbance data over the multiple absorbance measurement collection cycles.

In step 1720, the analyzer 140 calculates a concentration of the first gas type in the sample 126 based at least in part on an absorbance measurement obtained in the second cycle for the first frequency band and an absorbance measurement in the first cycle for the second frequency band.

In step 1730, the analyzer 140 calculates a concentration of the second gas type in the sample 126 based at least in part on an absorbance measurement obtained in the second cycle for the second frequency band and an absorbance measurement in the first cycle for the first frequency band.

FIG. 18 is a diagram of an example table 1810 illustrating different filters for use in a sample gas analyzer according to embodiments herein. As shown in table 1810, the one or more filters for detecting carbon monoxide can be centered around 4.651 microns and have a slightly tighter tolerance of 0.5%.

Those skilled in the art will understand that there can be many variations made to the operations of the user interface explained above while still achieving the same objectives of the invention. Such variations are intended to be covered by the scope of this invention. As such, the foregoing description of embodiments of the invention is not intended to be limiting. Rather, any limitations to embodiments of the invention are presented in the following claims.

What is claimed is:

1. A method comprising:
   generating an optical signal;
   at each of multiple frequency bands, measuring an intensity of the optical signal after passage of the optical signal through a sample gas having multiple types of gases that absorb the optical signal in a same frequency band; and
   detecting concentrations of the multiple types of gases in the sample gas based on absorption of the optical signal at the multiple frequency bands;
   wherein detecting concentrations of the multiple types of gases in the sample gas includes:
      utilizing absorbance measurements of the optical signal at a first frequency band and a second frequency band to calculate a concentration of a first gas present in the sample gas; and
      utilizing absorbance measurements of the optical signal at the first frequency band and the second frequency band to calculate a concentration of a second gas present in the sample gas.

2. The method as in claim 1, wherein measuring the intensity of the optical signal at each of multiple frequency bands includes:
   implementing a sequence of measuring absorbance of the sample gas at different frequency bands, the sequence including an absorbance measurement of the optical signal at the first frequency band followed by an absorbance measurement of the optical signal at the second frequency band followed by an absorbance measurement of the optical signal at a third frequency band; and
   initiating cyclical application of the sequence to repeatedly measure absorbance of the sample gas at the different frequency bands.

3. The method as in claim 2, wherein implementing the sequence includes:
   initiating rotation of an optical filter wheel assembly to align filters of the optical filter assembly in a path of the optical signal to filter the optical signal at the different frequency bands, the rotation of the optical filter assembly including aligning a first filter of the optical filter assembly in the path of the optical signal to measure absorbance by the sample gas at the first frequency band followed by aligning a second filter of the optical filter assembly in the path of the optical signal to measure absorbance by the sample gas at the second frequency band followed by aligning a third filter of the optical filter assembly in the path of the optical signal to measure absorbance by the sample gas at the third frequency band.

4. The method as in claim 1, wherein generating the optical signal includes:
   producing the optical signal as a modulated optical signal via serial application of different optical frequency band filters in a path of the optical signal.

5. The method as in claim 1, wherein measuring an intensity of the optical signal at each of multiple frequency bands includes repeatedly measuring absorbance of the optical signal by the sample gas at the multiple frequency bands over multiple absorbance measurement collection cycles; and
   wherein detecting the concentrations of the multiple types of gases in the sample gas includes successively approximating the concentrations of the multiple types of gases based on collection of absorbance data over the multiple absorbance measurement collection cycles.

6. The method as in claim 1, wherein measuring an intensity of the optical signal at each of multiple frequency bands includes:
   measuring absorbance of the optical signal by the sample gas at the multiple frequency bands in a first measurement cycle;
   subsequent to the first measurement cycle, measuring absorbance of the optical signal by the sample gas at the multiple frequency bands in a second measurement cycle; and
   wherein detecting concentrations of the multiple types of gases in the sample gas includes:
   calculating the concentrations based at least in part on absorbance measurements obtained in the first measurement cycle and absorbance measurements obtained in the second measurement cycle.

7. The method as in claim 1, wherein calculating the concentrations includes:

producing an absorbance measurement value by subtracting absorbance caused by an interfering gas from an absorbance measurement obtained at a particular frequency band; and utilizing the produced absorbance measurement value to calculate the concentration of the first gas.

8. The method as in claim 1 further comprising:

allocating the first frequency band of the multiple frequency bands to detect a concentration of a first gas type in the sample gas; and allocating the second frequency band of the multiple frequency bands to detect a concentration of a second gas type in the sample gas.

9. The method as in claim 8, wherein measuring an intensity of the optical signal at each of multiple frequency bands includes:

measuring absorbance of the optical signal by the sample gas at the first frequency band and the second frequency band in a first measurement cycle;

subsequent to the first measurement cycle, measuring absorbance of the optical signal by the sample gas at the first frequency band and the second frequency band in a second measurement cycle; and wherein detecting concentrations of the multiple types of gases in the sample gas includes:

calculating a concentration of the first gas type in the sample gas based at least in part on an absorbance measurement obtained in the second measurement cycle for the first frequency band and an absorbance measurement in the first measurement cycle for the second frequency band; and calculating a concentration of the second gas type in the sample gas based at least in part on an absorbance measurement obtained in the second measurement cycle for the second frequency band and an absorbance measurement in the first measurement cycle for the first frequency band.

10. The method as in claim 1, wherein measuring the intensity of the optical signal at each of multiple frequency bands includes:

measuring an intensity of the optical signal in a first frequency band, the first frequency band including optical energy at a wavelength around 5.2 micrometers;

measuring an intensity of the optical signal in a second frequency band, the second frequency band including optical energy at a wavelength around 4.6 micrometers.

11. The method as in claim 10, wherein measuring the intensity of the optical signal at each of multiple frequency bands includes:

measuring an intensity of the optical signal in a third frequency band, the third frequency band including optical energy at a wavelength around 7.8 micrometers.

12. A method comprising:

generating an optical signal;

at each of multiple frequency bands, measuring an intensity of the optical signal after passage of the optical signal through a sample gas having multiple types of gases that absorb the optical signal in a same frequency band;

detecting concentrations of the multiple types of gases in the sample gas based on absorption of the optical signal at the multiple frequency bands; and wherein measuring the intensity of the optical signal at each of multiple frequency bands includes:

measuring an intensity of the optical signal in a first frequency band, the first frequency band including optical energy at a wavelength around 2.5 micrometers;

measuring an intensity of the optical signal in a second frequency band, the second frequency band including optical energy at a wavelength around 4.6 micrometers;

measuring an intensity of the optical signal in a third frequency band, the third frequency band including optical energy at a wavelength around 4.8 micrometers;

measuring an intensity of the optical signal in a fourth frequency band, the fourth frequency band including optical energy at a wavelength around 5.2 micrometers;

measuring an intensity of the optical signal in a fifth frequency band, the fifth frequency band including optical energy at a wavelength around 6.2 micrometers; and measuring an intensity of the optical signal in a sixth frequency band, the sixth frequency band including optical energy at a wavelength around 3.2 micrometers.

13. A method comprising:

generating an optical signal;

at each of multiple frequency bands, measuring an intensity of the optical signal after passage of the optical signal through a sample gas having multiple types of gases that absorb the optical signal in a same frequency band; and detecting concentrations of the multiple types of gases in the sample gas based on absorption of the optical signal at the multiple frequency bands;

wherein measuring the intensity of the optical signal at each of multiple frequency bands includes:

measuring an intensity of the optical signal in a first frequency band to detect a concentration of water in the sample gas, the first frequency band including optical energy at a wavelength around 2.5 micrometers;

measuring an intensity of the optical signal in a second frequency band to detect a concentration of carbon monoxide in the sample gas, the second frequency band including optical energy at a wavelength around 4.6 micrometers;

measuring an intensity of the optical signal in a third frequency band to detect a concentration of carbon dioxide in the sample gas, the third frequency band including optical energy at a wavelength around 4.8 micrometers;

measuring an intensity of the optical signal in a fourth frequency band to detect a concentration of nitric oxide in the sample gas, the fourth frequency band including optical energy at a wavelength around 5.2 micrometers;

measuring an intensity of the optical signal in a fifth frequency band to detect a concentration of nitrogen oxide in the sample gas, the fifth frequency band including optical energy at a wavelength around 6.2 micrometers; and measuring an intensity of the optical signal in a sixth frequency band to detect a concentration of methane in the sample gas, the sixth frequency band including optical energy at a wavelength around 3.2 micrometers.

14. A system comprising:

an optical source to generate an optical signal;

a detector to measure an intensity of the optical signal after passing of the optical signal through a sample gas; and an analyzer to detect which of multiple gases are present in the sample gas based on measuring absorbance of the optical signal by the sample gas at different optical frequency bands, at least two gases of the multiple gases absorbing the optical signal in a same frequency band;

wherein the analyzer is configured to:

utilize absorbance measurements of the optical signal at a first frequency band and a second frequency band to calculate a concentration of a first gas present in the sample gas; and utilize absorbance measurements of the optical signal at the first frequency band and a third frequency band to calculate a concentration of a second gas present in the sample gas.

15. The system as in claim 14, wherein the analyzer is configured to:
implement a sequence of measuring absorbance of the sample gas at different frequency bands, the sequence including an absorbance measurement of the optical signal at the first frequency band followed by an absorbance measurement of the optical signal at the second frequency band followed by an absorbance measurement of the optical signal at the third frequency band; and
initiate cyclical application of the sequence to repeatedly measure absorbance of the sample gas at the different frequency bands.

16. The system as in claim 15 further comprising:
an optical filter wheel assembly including multiple filters; and
wherein the analyzer is configured to initiate rotation of the optical filter wheel assembly to align the filters of the optical filter assembly in a path of the optical signal to filter the optical signal at the different frequency bands.

17. The system as in claim 14 further comprising:
a controller configured to produce the optical signal as a modulated optical signal via serial application of different optical frequency band filters in a path of the optical signal.

18. The system as in claim 14, wherein the analyzer is configured to:
repeatedly measure absorbance of the optical signal by the sample gas at the multiple frequency bands over multiple absorbance measurement collection cycles; and
successively approximate the concentrations of the multiple types of gases based on collection of absorbance data over the multiple absorbance measurement collection cycles.

19. The system as in claim 14, wherein the analyzer is configured to:
measure absorbance of the optical signal by the sample gas at the multiple frequency bands in a first measurement cycle;
subsequent to the first measurement cycle, measure absorbance of the optical signal by the sample gas at the multiple frequency bands in a second measurement cycle; and
calculate the concentrations based at least in part on absorbance measurements obtained in the first measurement cycle and absorbance measurements obtained in the second measurement cycle.

20. The system as in claim 19, wherein the analyzer is configured to:
produce an absorbance measurement value by subtracting an absorbance measurement obtained in the first measurement cycle from an absorbance measurement obtained in the second measurement cycle; and
utilize the produced absorbance measurement value to calculate a concentration of a first gas of the multiple types of gases in the sample gas.

21. A system comprising:
an optical source to generate an optical signal;
a detector to measure an intensity of the optical signal after passing of the optical signal through a sample gas; and
an analyzer to detect which of multiple gases are present in the sample gas based on measuring absorbance of the optical signal by the sample gas at different optical frequency bands, at least two gases of the multiple gases absorbing the optical signal in a same frequency band;
wherein the analyzer is configured to:
produce an absorbance measurement value by subtracting an absorbance measurement obtained in the first measurement cycle from an absorbance measurement obtained in the second measurement cycle; and
utilize the produced absorbance measurement value to calculate a concentration of a first gas of the multiple types of gases in the sample gas;
wherein the analyzer is configured to:
measure absorbance of the optical signal by the sample gas at the first frequency band and the second frequency band in a first measurement cycle;
subsequent to the first measurement cycle, measure absorbance of the optical signal by the sample gas at the first frequency band and the second frequency band in a second measurement cycle;
calculate a concentration of the first gas type in the sample gas based at least in part on an absorbance measurement obtained in the second measurement cycle for the first frequency band and an absorbance measurement in the first measurement cycle for the second frequency band; and
calculate a concentration of the second gas type in the sample gas based at least in part on an absorbance measurement obtained in the second measurement cycle for the second frequency band and an absorbance measurement in the first measurement cycle for the first frequency band.

22. A computer program product including a non-transitory computer-readable media having instructions stored thereon for processing data information, such that the instructions, when carried out by one or more processing devices, enables the one or more processing device to perform operations of:
generating an optical signal;
at each of multiple frequency bands, measuring an intensity of the optical signal after passing of the optical signal through a sample gas having multiple types of gases that absorb the optical signal in a same frequency band; and
detecting concentrations of the multiple types of gases in the sample gas based on absorption of the optical signal at the multiple frequency bands;
wherein detecting concentrations of the multiple types of gases in the sample gas includes:
utilizing absorbance measurements of the optical signal at a first frequency band and a second frequency band to calculate a concentration of a first gas present in the sample gas; and
utilizing absorbance measurements of the optical signal at the first frequency band and the second frequency band to calculate a concentration of a second gas present in the sample gas.

* * * * *